United States Patent [19]

Kieturakis

[11] Patent Number: 5,591,191
[45] Date of Patent: Jan. 7, 1997

[54] SURGICAL INSTRUMENT AND METHOD FOR HELICALLY INCISING A PATHWAY INTO THE INTERIOR OF THE BODY

[76] Inventor: Maciej J. Kieturakis, 372 Beverly Dr., San Carlos, Calif. 94070

[21] Appl. No.: 316,164

[22] Filed: Sep. 30, 1994

Related U.S. Application Data

[63] Continuation-in-part of Ser. No. 187,753, Jan. 26, 1994, abandoned.

[51] Int. Cl.[6] .................................................. A61M 29/00
[52] U.S. Cl. ............................................ 606/185; 604/164
[58] Field of Search ...................................... 606/108, 167, 606/170, 184, 185; 604/110, 117, 160–169, 185, 189, 246–248, 264, 272, 274, 283

[56] References Cited

U.S. PATENT DOCUMENTS

| | | |
|---|---|---|
| 4,191,191 | 3/1980 | Auburn . |
| 4,535,773 | 8/1985 | Yoon . |
| 4,601,710 | 7/1986 | Moll . |
| 4,654,030 | 3/1987 | Moll et al. . |
| 5,116,353 | 5/1992 | Green . |
| 5,147,316 | 9/1992 | Castillenti . |
| 5,147,376 | 9/1992 | Pianetti . |
| 5,203,773 | 4/1993 | Green . |
| 5,209,736 | 5/1993 | Stephens et al. . |
| 5,224,952 | 7/1993 | Deniega et al. . |
| 5,226,890 | 7/1993 | Ianniruberto et al. . |
| 5,232,451 | 8/1993 | Freitas et al. . |
| 5,258,003 | 11/1993 | Ciaglia et al. . |
| 5,271,380 | 12/1993 | Riek et al. . |
| 5,279,567 | 1/1994 | Ciaglia et al. . |

*Primary Examiner*—Michael Powell Buiz
*Assistant Examiner*—William Lewis
*Attorney, Agent, or Firm*—Skjerven, Morrill, MacPherson, Franklin & Friel; Norman R. Klivans

[57] ABSTRACT

A surgical incising instrument having a helical blade allows a surgeon to helically incise a pathway through tissue into the interior of the body at a controlled rate without exerting longitudinal forces on the instrument. The instrument incorporates a variform or "split-lands" helix that includes a blade member with a sharp helical blade edge and a shield member with a dull helical edge that mate along helicoidal interfaces that "split" the lands, thus providing for a helix periphery that may either expose or not expose the sharp blade edge outside the dull lands. The instrument is particularly useful for accessing an anatomic cavity and incorporates a latch and spring mechanism that transforms the variform helix into a dull-edged helix from a sharp-edged helix in response to penetration of a body wall overlying an anatomic cavity, thus protecting organs within the cavity from contact with any sharp blade edge.

27 Claims, 16 Drawing Sheets

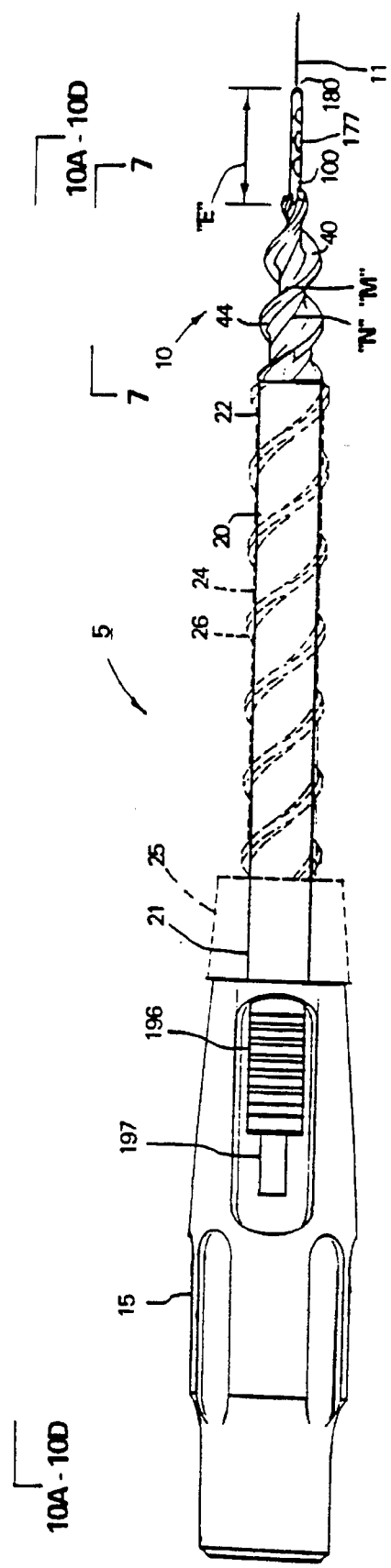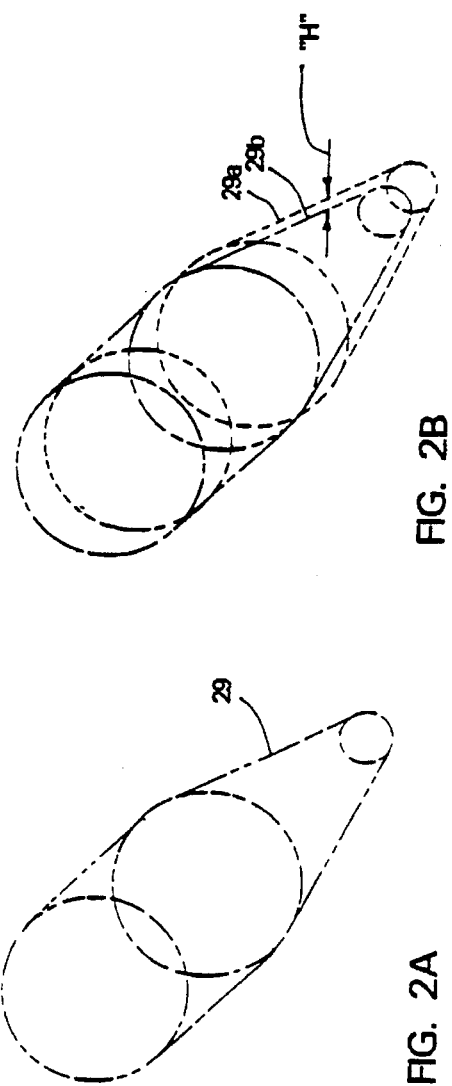

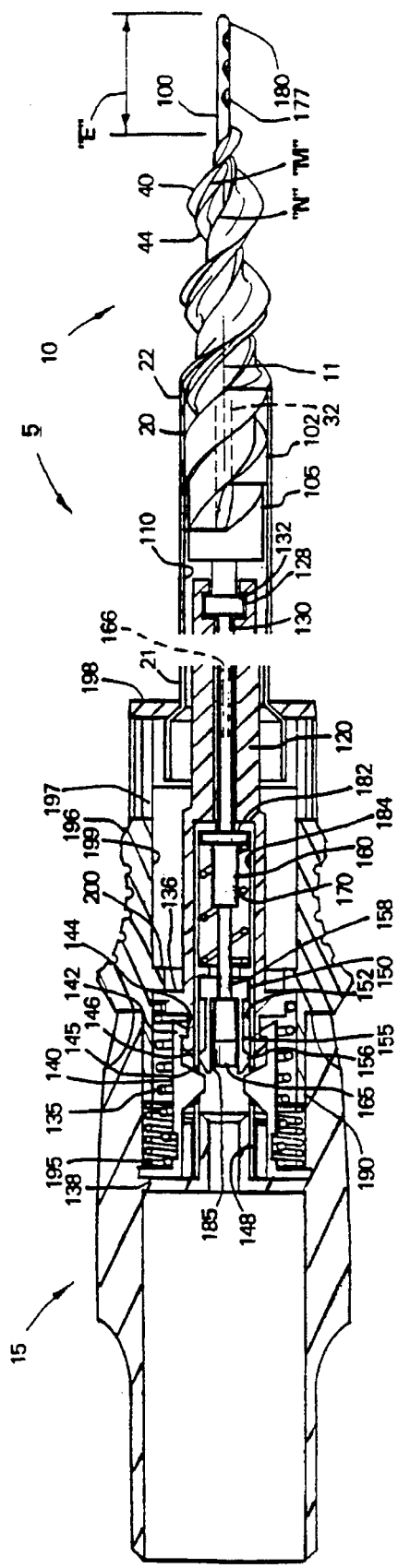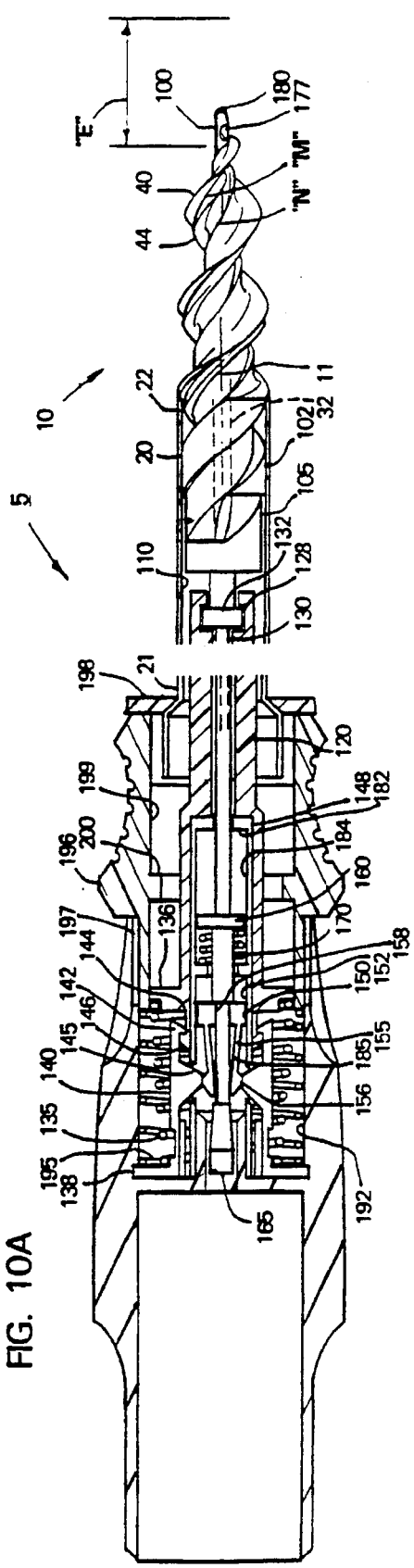
FIG. 10A
FIG. 10B

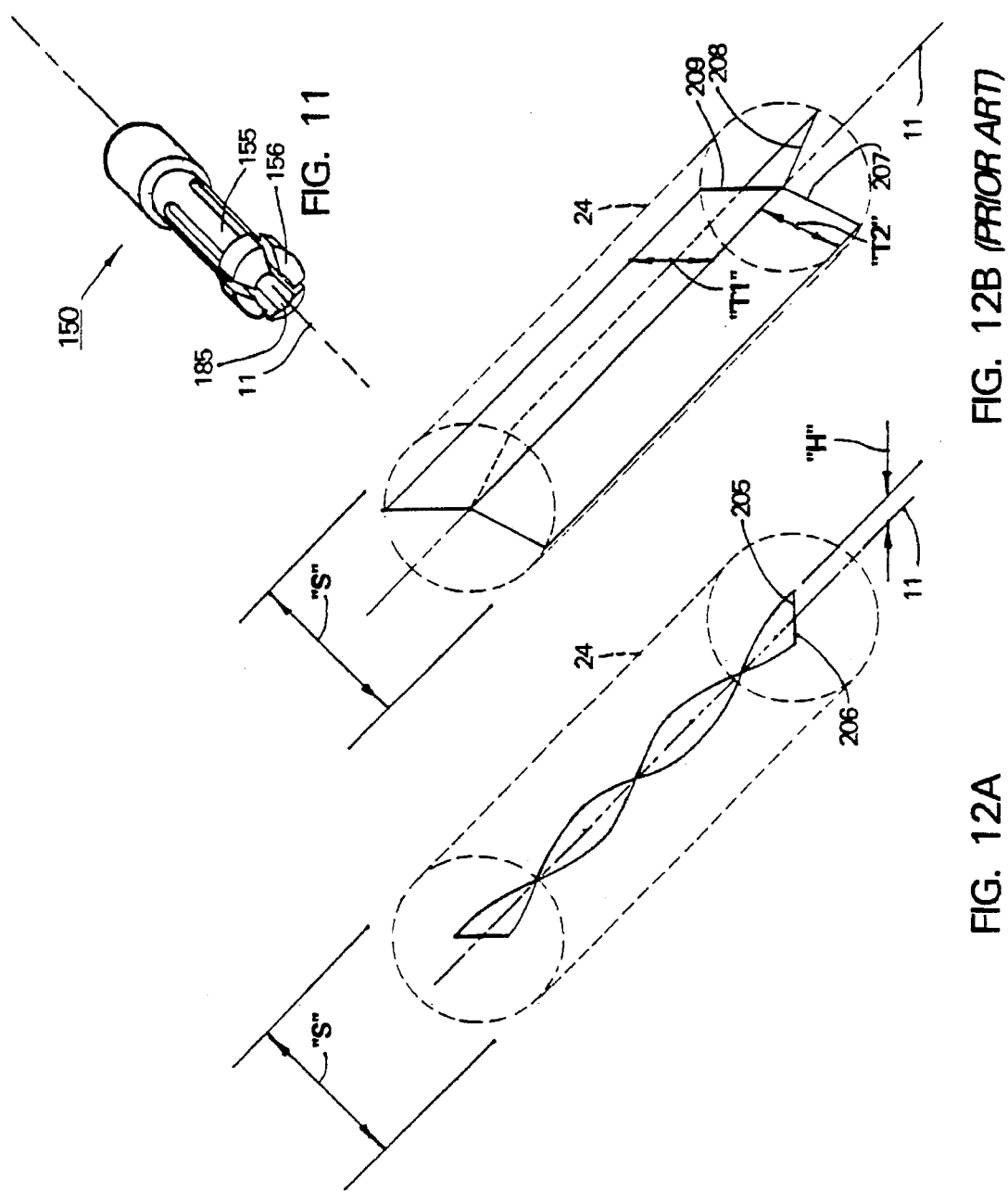

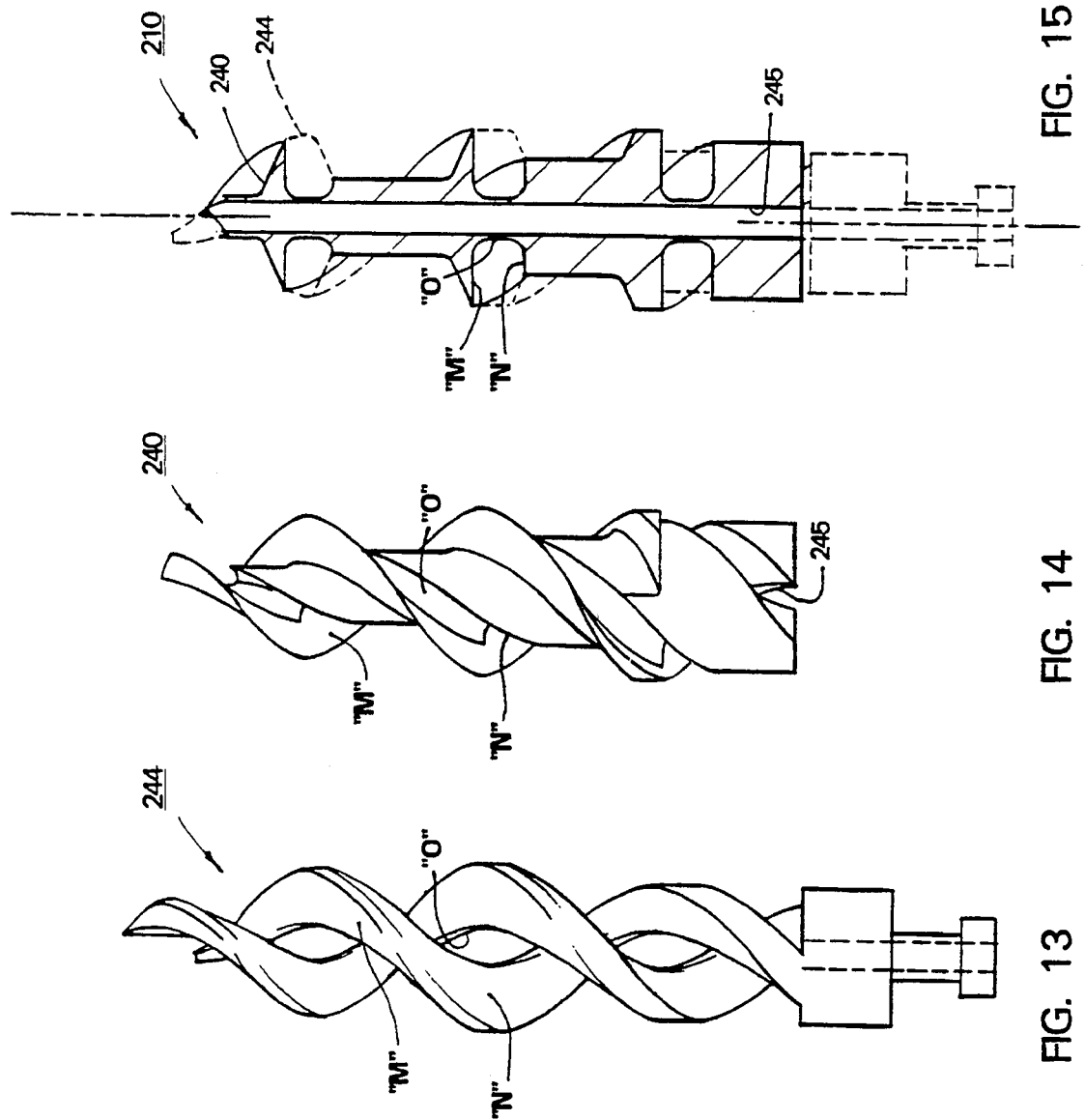

SURGICAL INSTRUMENT AND METHOD FOR HELICALLY INCISING A PATHWAY INTO THE INTERIOR OF THE BODY

CROSS-REFERENCE TO RELATED APPLICATION

This application is a continuation-in-part of U.S. patent application Ser. No. 08/187,753 filed Jan. 26, 1994 now abandoned. This application also is related to copending and commonly invented application Ser. No. 08/255,273 filed Jun. 1, 1994.

BACKGROUND OF THE INVENTION

1. Field of the Invention

This invention relates to surgical instrumentation for incising tissue in a human body and more particularly to an instrument and method for incising a pathway through tissue overlying an anatomic cavity or region of lesser density and for placing a cannula within the incised pathway to provide access to the interior of the body.

2. Description of Prior Art

Surgical techniques employing endoscopes and accessory instruments introduced into the interior of the body through cannulas have become increasingly important in a field known as "endoscopic" surgery. A surgeon performing an endoscopic surgery in the abdominal cavity first inserts a Verress needle through the abdominal wall and insufflates the cavity with ($CO_2$) gas to separate the wall from the internal organs. Trocars and other cutting instruments have been provided for puncturing or cutting a pathway through tissue overlying the abdominal cavity for cannula placement.

A trocar is a shafted instrument with a sharp tip that is used to puncture a pathway through tissue. Commercially available trocars typically are configured with a three-faced pyramidal piercing tip from which the name trocar is derived: trois (three) and carre (sides or faces). Trocars suffer from the disadvantage of requiring powerful thrusting forces to puncture a path through tissue. The sharp tip and edges of the trocar can cause injury to an internal organ upon the slightest contact. Attempts to shield trocar tips within reciprocating sleeves after penetration into an anatomic cavity are undesirable because such sharp tips must pierce fully into the cavity before the shielding sleeve is triggered.

Other cutting instruments for abdominal access rely on screw threads to reduce the required thrusting forces, but such instruments offer no shielding for their sharp tips after penetration into the abdominal cavity. Such threaded instruments rely on precautionary insufflation as the only means to prevent lacerations of internal organs as their sharp tips penetrate the abdominal wall. There is therefore a need for new instruments and methods for safely incising a path through tissue and more particularly for incising a pathway through the abdominal wall with or without insufflation of the abdominal cavity and for placing a cannula within the incised pathway.

SUMMARY OF THE INVENTION

The present invention relates to a helical incising instrument and method that allows a surgeon to incise a pathway through tissue into the interior of the body at a controlled rate without exerting longitudinal forces on the instrument. The instrument is particularly useful for accessing an anatomic cavity or other region of lesser tissue density. The instrument has a helical blade edge that is capable of transformation from sharp to dull, or from an "incising" configuration to a "non-incising" configuration, that is responsive to penetration of a body wall overlying an anatomic cavity. The transformation of the helical blade from sharp to dull serves to protect organs within the anatomic cavity from contact with any sharp blade edge.

The helical endoscopic pathway cutter, hereafter "heliscopic cutter," has a variform or "split-lands" helix that is formed of two mating components: a blade member with a sharp helical blade edge and a shield member with a dull helical edge or lands. The blade member and shield member mate along a constant spiral lead helicoidal interface that "splits" the lands at one edge of the lands. In this regard, the blade member and shield member may travel helically relative to one another along the helicoidal interfaces about the axis of the helix. Both the blade and shield members have tapered envelopes or peripheries (blade periphery and lands periphery) that are in registration in the non-incising configuration so that the sharp blade edges are not exposed outside the lands. As the blade and shield members travel helically a slight amount, the blade periphery will be slightly exposed radially outward from the lands periphery to provide an "incising" configuration having a razor-sharp blade edge capable of incising tissue. The helical travel of the blade member relative to the shield member between the "incising" and "non-incising" configurations is smooth and seamless and may be almost imperceptible to the eye. The principal underlying the transformation of a dull helical edge to a sharp helical edge is the relative movement of two tapered peripheries in and out of registration—not by axial movement—but by relative helical movement of the members along helicoidal interfaces.

An exemplary instrument that incorporates a variform helix is an abdominal heliscopic cutter that includes:

(a) an elongate introducer sleeve carrying a variform incising helix at its distal (far) end that is transformable between "incising" and "non-incising" positions;

(b) a tissue-displacing structure incorporated into the variform helix adapted to displace tissue perpendicularly outward from the axis of the incised pathway to accommodate a cannula;

(c) a transforming mechanism with a latch mechanism that biases the variform helix to the non-incising position from the incising position; and (d) a reciprocating probe member responsive to counterforce applied to its distal end that serves as a trip mechanism to release the latched transforming mechanism after the helix penetrates into an anatomic cavity or region of lesser density.

In an exemplary method, assume the surgeon wishes to incise a pathway into the abdominal cavity and place a cannula within the pathway. The heliscopic cutter is inserted into a cannula assembly. The heliscopic cutter, and more particularly the variform helix, is "armed" to the incising configuration by sliding an arming grip in a proximal direction thus engaging a latch mechanism to maintain the helix in the sharp incising configuration.

The surgeon grasps the instrument handle and presses the tip of the heliscopic cutter, in particular the distal end of the probe, into a small incision made in the skin of the abdominal wall. The counterforce exerted by the tissue causes the probe to retract. As the distalmost blade edge contacts the abdominal wall, the surgeon rotates the handle helically, advancing the instrument into and through the tissue. As the distalmost blade edge contacts the inner membrane of the abdominal wall and begins to incise an arc in the inner membrane, counterforce is relaxed against the probe tip allowing the probe to project distally into the abdominal cavity under the force of a spring. The distal projection of the probe serves as a trip mechanism to disengage the latch which causes a spring to instantly transform the variform helix to the non-incising configuration, thus preventing any sharp blade edge from entering the abdominal cavity.

With the variform helix in the non-incising configuration, the helical periphery of the helix still engages tissue of the abdominal wall as a dull-edged screw. The surgeon continues to rotate the instrument thus expanding the diameter of the pathway to accommodate the cannula. After the helix is advanced into the abdominal cavity, the heliscopic cutter may be withdrawn from the cannula assembly leaving the cannula in place within the abdominal wall.

In general, the present invention provides a incising instrument and method for making a pathway through tissue that does not require the application of thrusting longitudinal forces as with puncturing trocars. The present invention also provides an instrument and method that applies forces that are only tangential to the axis of travel.

The present invention provides an instrument and method that utilizes a helical blade that allows a slow and controlled rate of advancement through tissue. The present invention also provides an instrument and method in which the incising helix has a "split lands" that is reconfigurable to a non-incising position from an incising position upon penetration into a body cavity. The present invention also provides an instrument and method that allows a surgeon to incise a pathway through an anatomic wall without a sharp blade entering into the anatomic cavity as a means of preventing inadvertent contact with internal organs.

The present invention provides an instrument and method that makes only shallow helical incisions in tissue that allow for rapid healing of blood vessels. The present invention also provides an instrument and method that expands the transverse dimension of the incised pathway to accommodate a cannula by displacing tissue perpendicularly from the pathway axis to further eliminate longitudinal pressures on tissue. The present invention also provides an instrument and method that allows the surgeon to lift the instrument proximally as it is rotated and embedded in tissue, thus lifting an anatomic wall away from contact with internal organs to further eliminate longitudinal pressures on tissue.

The present invention provides an instrument and method that may be used to access an anatomic cavity without prior time-consuming insufflation of the cavity. The present invention also provides an instrument and method for placing a cannula in an abdominal wall in approximately 1 to 2 minutes using a single instrument which is to be contrasted with current practices requiring 5 to 10 minutes using a Verress needle and a trocar.

Additional advantages and features of the invention appear in the following description in which several embodiments are set forth in conjunction with the accompanying drawings.

BRIEF DESCRIPTION OF THE DRAWINGS

FIG. 1 is an elevational view of the heliscopic cutter of the present invention incorporating a variform helix.

FIGS. 2A–2B are axionometric line illustrations of the surface envelopes or peripheries of the component parts of a variform helix in alternative positions.

FIGS. 10A–10D are a sequence of longitudinal partial sectional views of the internal mechanisms of the heliscopic cutter showing it in various stages of use.

FIG. 11 is an axionometric elevational view of the trigger of the heliscopic cutter.

FIG. 12A is an axionometric line illustration of the type of blade tracks made in tissue by a variform helix.

FIG. 12B is an axionometric line illustration of the type of cuts in tissue made by a puncturing trocar with a pyramidal cutting tip.

FIG. 13 is an elevational view of a de-mated shield member of a second embodiment of variform helix.

FIG. 14 is an elevational view of a de-mated blade member of the second embodiment of variform helix that mates with the shield member of FIG. 13.

FIG. 15 is a sectional view the blade member of FIG. 14 with the shield member of FIG. 13 in phantom view in a first (non-incising) position.

Figure 3:
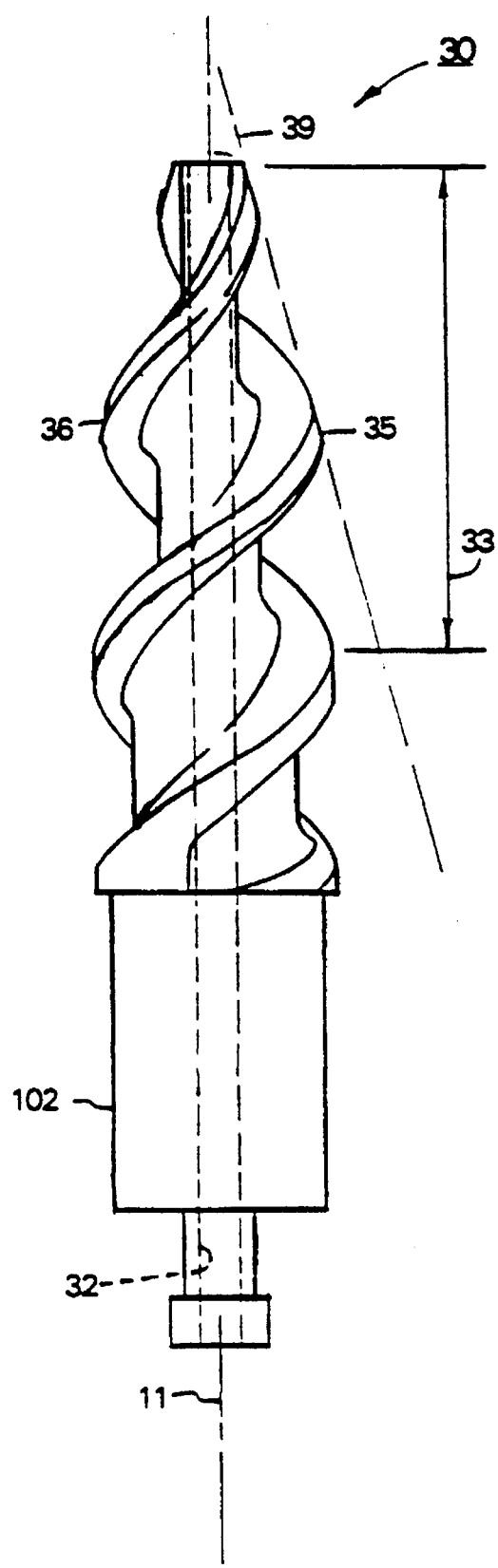
FIG. 3 is an elevational view of a helix blank from which a variform helix may be fabricated.

DESCRIPTION OF PREFERRED EMBODIMENT OF THE INVENTION.

By way of example, FIG. 1 depicts heliscopic cutting instrument 5 with a variform helix or "splitlands" helix 10 that is suitable for incising a pathway through a patient's abdominal wall for an abdominal endoscopic procedure.

More in particular, heliscopic cutting instrument 5 of the present invention is generally cylindrical in shape and extends along longitudinal axis 11 (see FIG. 1). Handle 15 of instrument 5 is made of any suitable material such as plastic and is adapted for gripping by a human hand. Cylindrical introducer sleeve 20 having proximal and distal ends, respectively 21 and 22, is coupled to handle 15. Introducer sleeve 20, described further below, is dimensioned to slide through standard-sized cannula 24, and sleeve 20 in the accompanying drawings is shown in 10 mm. diameter suitable for use with cannula assembly 25 (shown in phantom view in FIG. 1). Cannula 24 incorporates continuous helical threads 26 that correspond to the form of the variform helix.

Referring to FIG. 1, variform helix or "split-lands" helix 10 is coupled to distal end 22 of introducer sleeve 20. The variform helix 10 of FIG. 1 comprises mating components, or blade and shield members, that may be metal and may be fabricated by grinding, injection-molding or casting. Thin cross-section blade components may be formed from flat steel strip material. The component parts also may be made from injection-molded plastic that is capable of having a relatively sharp edge.

An exemplary method of fabricating the component parts of variform or split-lands helix 10 from a screw-shaped blank follows, which is instructional for describing the manner in which the component parts helically mate. It should be noted that the exemplary method utilizes wire EDM (electrical discharge machining) and may not be suitable for large-scale manufacturing of a variform helix. The EDM approach described herein, however, may be utilized in fabricating tooling or molds for large scale manufacturing of variform helixes.

The exemplary EDM method of making a split-lands helix also illustrates a principle involved in providing a helix that is variably formable between having a dull-edged helical periphery and a sharp-edged helical periphery. Referring to FIGS. 2A–2B, the capability of a variform helix to transform its periphery 29 derives from the manner in which its component parts, each having a tapered outer periphery or surface envelope represented in envelope outlines 29a and 29b, may be moved in and out of registration with one another not by axial movement, but by relative helical movement to provide radial exposure "H" between the tapered portions of the envelopes (see FIG. 2B).

Referring to FIG. 3, helix 10 may be fabricated from a dull or rounded-edge helical blank 30 that is made in the indicated tapered helical shape by grinding. The blank 30 is, for example, stainless steel 440C. Axial bore 32 extends along axis 11. The helical blank has double-start constant spiral lead 33 of 0.800" as measured along the taper (not limiting) with double-lead helical protruding regions 35 and 36. As depicted in FIG. 3, helical protrusions 35 and 36 extend approximately 720° (not limiting) around blank 30. The outermost periphery or envelope 39 that surrounds the helical protruding regions 35 and 36 exhibits a decreasing transverse cross-section (cone shape) in the distal direction.

Blank 30 may be machined into component parts to make the helix variform with a 6-axis wire EDM unit. By the term 6-axis, it is meant that the wire EDM has five commonly available (fully synchronized) axes, "X", "Y", "Z", "U" and "V". In addition, the wire EDM requires a fully synchronized sixth axis which is a rotational axis. For example, the technical center of Mitsubishi EDM and its subsidiary MC Machinery Systems, Inc. of Cypress, Calif. has a Mitsubishi Model DWC-110SZ wire EDM unit with an additional 6th rotational axis that is identified as a "B" axis.

Helical blank 30 is mounted in the "B" axis drive such that axis 11 of blank 30 is on centerline of the "B" axis' rotation. The EDM wire is preferably 0.003" diameter but wire diameters of up to 0.008" are satisfactory for fabricating exemplars of the variform helix. The EDM wire is held on the "Z" axis at 90° relative to the "B" axis. The "Y" axis is also aligned with axis 11 of blank 30 and the "B" axis' rotation. The "Y" and "B" axes are programmed to move in a synchronized manner both axially and angularly (i.e., helically) to "burn" or cut a constant spiral lead through blank 30. The "X", "Z", "U" and "V" axes are programmed to not move.

Figure 4:
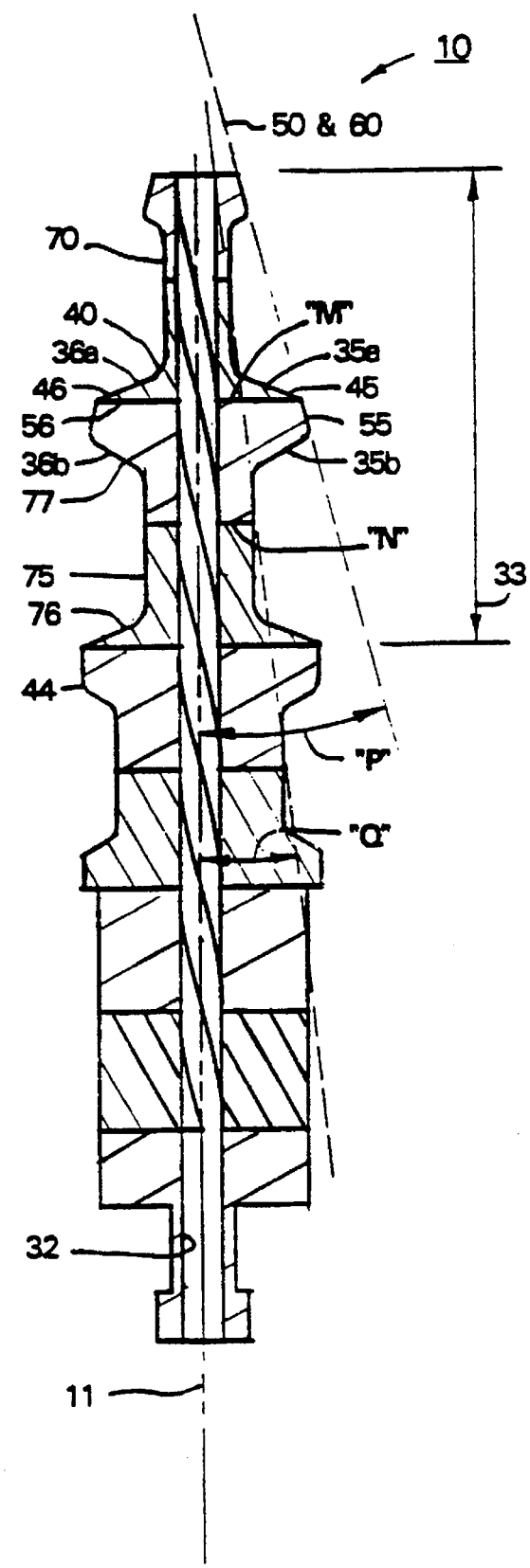
FIG. 4 is a longitudinal sectional view of a variform or "split-lands" helix fabricated from a blank similar to that shown in FIG. 3.

Before commencing the burn, the distal end of blank 30 is aligned with the EDM wire such that helical protrusions 35 and 36 are aligned with the EDM wire to burn a path, for example, at the distal outermost edge of the helical protrusions 35 and 36. Thereafter, the "Y" and "B" axes advance blank 30 through the EDM wire which results in a burn path labeled burn "M" in FIG. 4 and yields corresponding helicoidal surfaces on either side of the burn path. After advancing blank 30 approximately 540° (not limiting) through the EDM wire, the "Y" axis is stopped while the "B" axis is rotated by approximately 90° (not limiting) thus burning a straight cut around axis 11, resulting in a 0.400" longitudinal offset from the path of burn "M" (one-half of the spiral lead as shown in FIG. 4, but such dimension is not limiting). Thereafter, the previous synchronized "Y" and "B" axis program is repeated in reverse to burn another helical burn path labeled "N" out of blank 30.

Referring to FIG. 4, the result of the previously described EDM burns through paths "M" and "N" yields component parts that helically mate along helicoidal surfaces on either side of the burn paths, now alternatively called helicoidal interfaces "M" and "N". In other words, the helical protrusion 35 is "split" into portions 35a and 35b that lie on either side of interface "M". Likewise, helical protrusion 36 is "split" into portions 36a and 36b that lie on either side of interface "M". The component parts also helically mate along interface "N" which lies midway (not limiting) between the intertwining parts of interface "M". The component parts may be de-mated by helically separating one from the other.

Having described an exemplary method of fabricating a variform or "split-lands" helix, it now is possible to further identify elements of the component parts to better describe the manner in which the helix transforms its helical protrusions, 35 and 36, from sharp to dull.

Referring to FIG. 4, variform helix 10 now is depicted with its two interfitting members: a helical blade member 40 (or "blade") and a helical shield member 44 (or "shield"). Blade and shield respectively 40 and 44 interfit and slidably mate along helicoidal interfaces, "M" and "N". Such helicoidal interfaces, "M" and "N", may be defined as the warped surface or plane generated by a line extending from axis 11 outwardly as the line passes through all points of a helix disposed around axis 11. In FIG. 4, such helicoidal interfaces, "M" and "N", between blade 40 and shield 44 are generated by constant spiral lead 33 of approximately 0.800", but such spiral lead may range from e.g. less than 0.200" to 2.00" or more. Spiral lead 33 may be defined as the axial travel resulting from an angular movement of 360° of the line extending from the axis outwardly as the line passes through a helix around axis 11, and as such, spiral lead 33 is generally equal to the axial travel of variform helix 10 in tissue through 360° rotation. In FIG. 4, the variform helix has double-lead configuration with helical protrusions 35 and 36, but it should be appreciated that a variform helix may have a single-lead or plural-lead and fall within the scope of the present invention.

Figure 5:
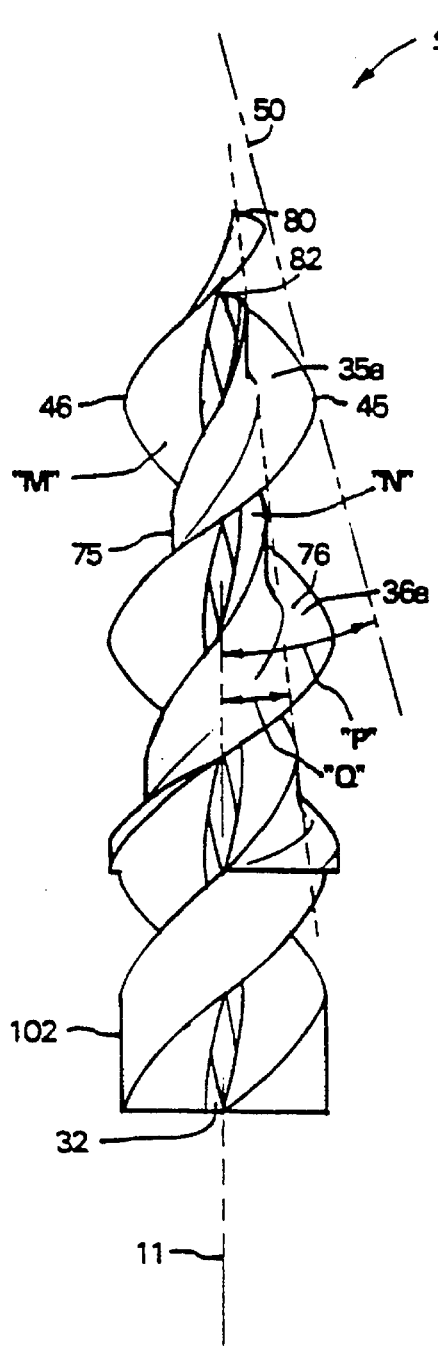
FIG. 5 is an elevational view of the de-mated blade member of the variform or "split-lands" helix of FIG. 4.

More specifically referring to FIG. 5, helical blade 40 is shown de-mated, which is actually two elements but will be referred to hereafter as a singular member. The double-lead helical protrusions in blade member 40 now are helical portions 35a and 36a. The helical portions 35a and 36a have outermost edges herein called blade edges respectively 45 and 46 that are sharp and capable of incising tissue. The blade edges 45 and 46 are circumscribed by a blade envelope or periphery 50. Blade periphery 50 of blade 40 exhibits a decreasing transverse cross-section (taper) toward the distal direction and tapers at inclusive angle "P" of approximately 14° in the accompanying drawings, but such dimension is not limiting and such inclusive angle may range from e.g. less than 5° to 40° or more. Blade periphery 50 typically is cone-shaped but may be tapered in a bullet-shape or ball-end shape.

Figure 6:
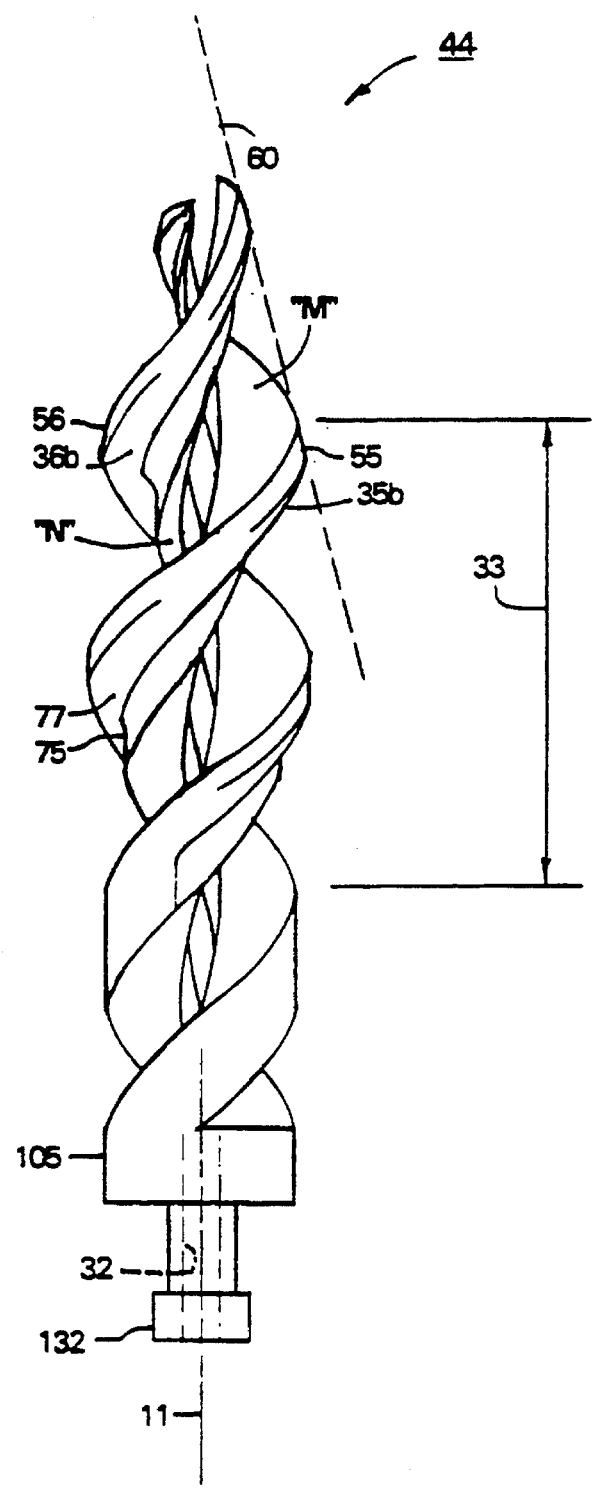
FIG. 6 is an elevational view of the de-mated shield member of the variform or "split-lands" helix of FIG. 4.

Specifically referring to FIG. 6, helical shield member 44 with helical protrusions 35b and 36b is shown de-mated. The outer radial edge of helical protrusions 35b and 36b exhibit lands 55 and 56 that are flat, rounded or generally dull and incapable of incising tissue. The outer periphery of lands 55 and 56 are circumscribed by shield envelope or periphery 60. Shield periphery 60 of shield 44 exhibits a decreasing transverse cross-section or tapers at inclusive angle "P" which corresponds to blade periphery 50.

Figure 7:
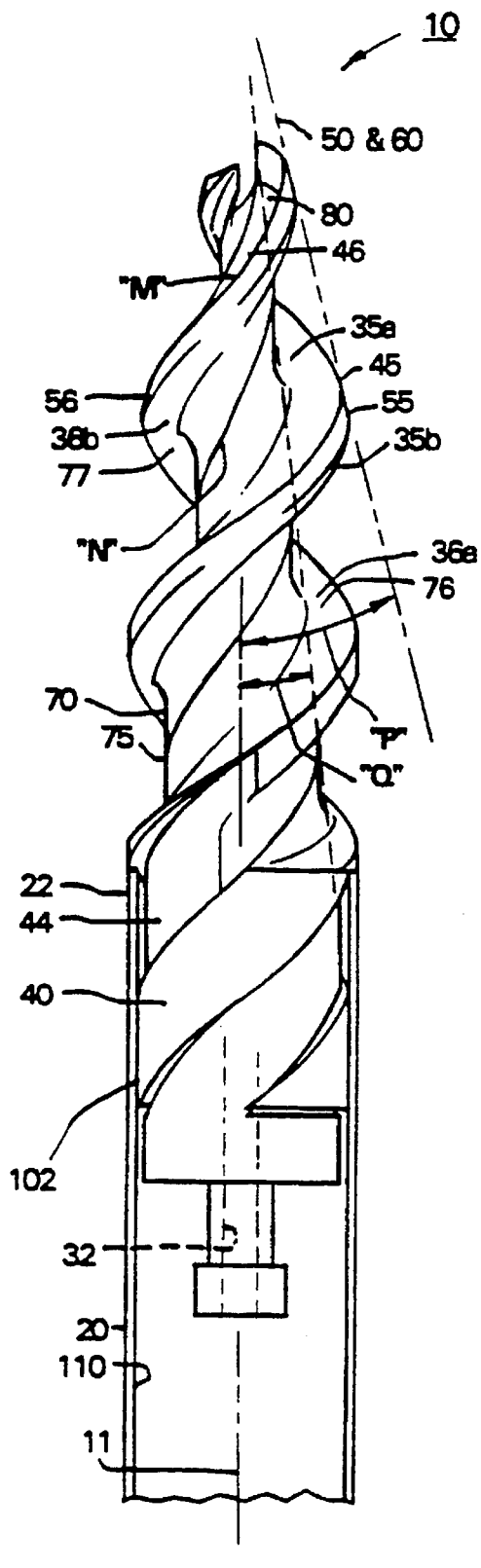
FIG. 7 is an elevational view of the variform or "split-lands" helix of FIG. 4 taken along line 7—7 of FIG. 1 in the non-incising position.
Figure 8:
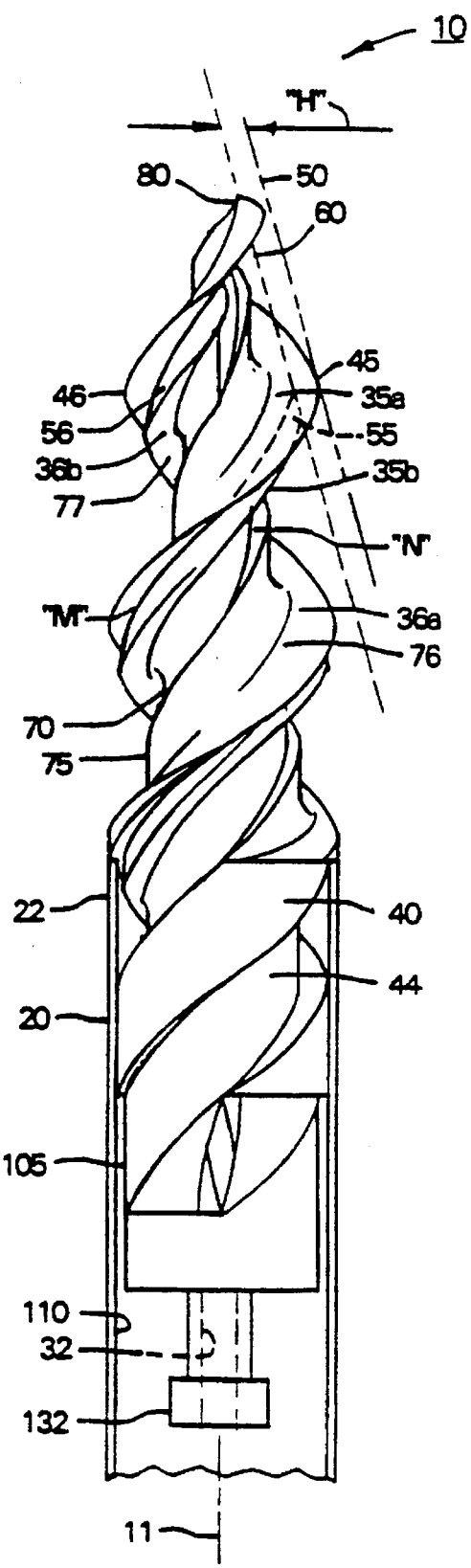
FIG. 8 is an elevational view of the variform or "split-lands" helix of FIG. 7 in the incising position.

Referring to FIGS. 7–8, it now can be seen that blade member 40 and shield member 44 may travel helically relative to each other generally around axis 11 to make variform helix 10 transformable between a non-incising position (see FIGS. 4 and 7), and an incising position (see FIG. 8). Referring to helix 10 depicted in FIG. 8 in the incising position, the blade periphery 50 is exposed radially outward and beyond shield periphery 60 a distance called herein blade exposure "H" thus providing a helix with a razor-sharp helical blade edge. Conversely, as shown in FIGS. 4 and 7, helical lands 55 and 56 of shield 44 serve to shield the sharp blade edges 45 and 46 when the helix is in the non-incising position. To make a variform helix capable of incising a pathway, the helical blade edges 45 and 46 need only be exposed very slightly (blade exposure "H") beyond lands 55 and 56, for example as little as 0.020", to accomplish the objective of incising a pathway. The accompanying drawings illustrate a somewhat exaggerated blade exposure "H" for purposes of clarity, and exemplary "H" dimensions ranging from 0.010" to 0.150" are not limiting for various diameter variform helixes.

For displacing tissue radially outward from the axis of the pathway to accommodate the diameter of cannula 24, there are two helical channels 70 (collectively) between helical protrusions, 35 and 36. Referring again to FIGS. 4 and 7, the helical channels 70 are best seen in a mated variform helix 10 in the non-incising configuration. A portion of a helical channel 70 is for instance formed into each blade member 40 and shield member 44 but this is not limiting. The helical channel 70 is configured with inner face 75, proximal face 76 and distal face 77. The channel inner face 75 generally is parallel to axis 11 for reasons explained hereinbelow although varied inner face angles are possible. The inner face also may be contoured or radiused into the proximal and distal faces, respectively 76 and 77. The proximal and distal faces 76 and 77 display somewhat angular surfaces with respect to axis 11 that may range from approximately 30° to 90°. The radial dimension from channel inner face 75 to blade or lands periphery, 50 or 60, may range from 0.00" to 0.500" or more and such dimension will vary over the length the variform helix depending on the helix diameter. The inner face 75 of helical channel 70 exhibits a decreasing transverse cross-section in the distal direction wherein the inclusive angular rise "Q" of the inner face 75 relative to axis 11 is shown as 7° but may range from approximately 4° to 40° when such angular rise "Q" is measured from the distal end of helix 10 to the midpoint of channel 70.

It should be appreciated that the longitudinal sectional dimension of blade member 40 may vary from thin to thick with shield member 44 having a cooperating sectional dimension. In helix 10 illustrated herein, the blade 40 and shield 44 have approximately equal longitudinal sectional dimensions as when the members are made from rigid stainless steel or plastic. However, the blade member may have a thin longitudinal sectional dimension, for example of 0.004" to 0.009" as in razor blade strip material, with helicoidal interfaces "M" and "N" lying on either side of the thin section, in which case channel 70 would be formed entirely within the shield member.

In the accompanying drawings, double-lead blade member 40 has a blade edge 45 that exhibits a distal leading edge 80 (see FIG. 5) relative to blade edge 46 that has a lagging edge 82 for reasons explained hereinbelow. It should be appreciated, however, that a plural-lead blade member 40 may display distalmost blade edges that do not lead and lag, and such plural blades may be angularly spaced apart from approximately 0° to 180° and be within the scope of the present invention.

The selection of spiral lead 33, shape and angle "P" of blade and shield peripheries, 50 and 60, blade exposure "H" and angular rise "Q" of the channel inner face 75 are interrelated and dependent upon surgical objectives and considerations. These considerations include the diameter of introducer sleeve 20, the required depth of the incised pathway, the density of the tissue through which the pathway will extend and the desired helical travel of blade 40 relative to shield 44 between the incising and non-incising positions.

FIGS. 9A–9F now diagrammatically illustrate the variform helix of the present invention as it appears in various stages of incising a pathway through an abdominal wall. Cannula 24 with cannula threads 26 is dimensioned to interfit with instrument 5 as shown in the illustrations.

Figure 9A:
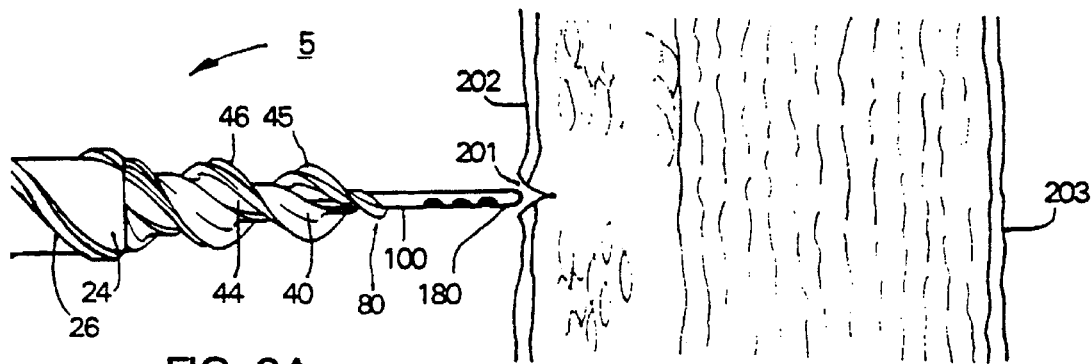
FIGS. 9A–9F are a sequence of cut-away views showing the variform helix of the present invention in various stages of use in incising a pathway through a patient's abdominal wall.

In the initial or rest position (see FIG. 1), the blade 40 and shield 44 of the helix are in the non-incising position with the reciprocating probe 100 extended outward (distally) beyond the distal end of the helix under the influence of a spring. Referring to FIG. 9A, instrument 5 is depicted "armed" and prepared to helically incise a pathway in an abdominal wall 202. In other words, the helical blade edges, 45 and 46, exhibit blade exposure "H" slightly radially outward from cooperating helical lands, 55 and 56. The helix is maintained in the armed position by a latch mechanism described in detail below.

Figure 9B:
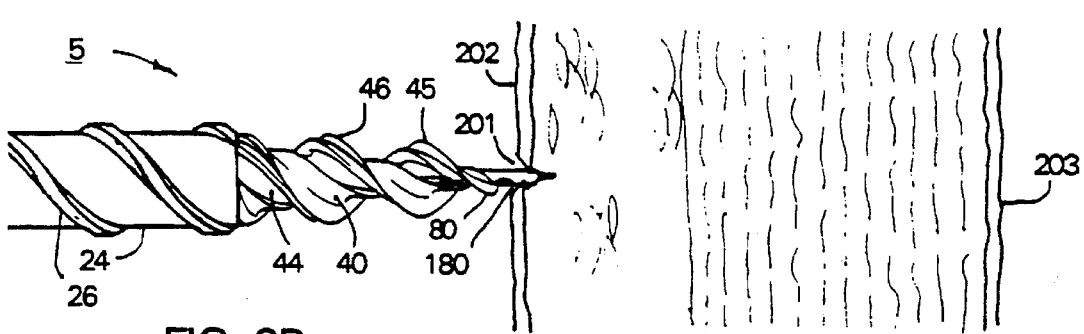

Referring to FIG. 9B, as the reciprocating probe is pressed into a small incision 201 in the abdominal wall 202, the counterforce against the probe tip 180 urges the probe 100 inward (proximally) to a retracted position. The later distal projection of probe 100 will trip the latch mechanism to disarm the helix.

Figure 9C:
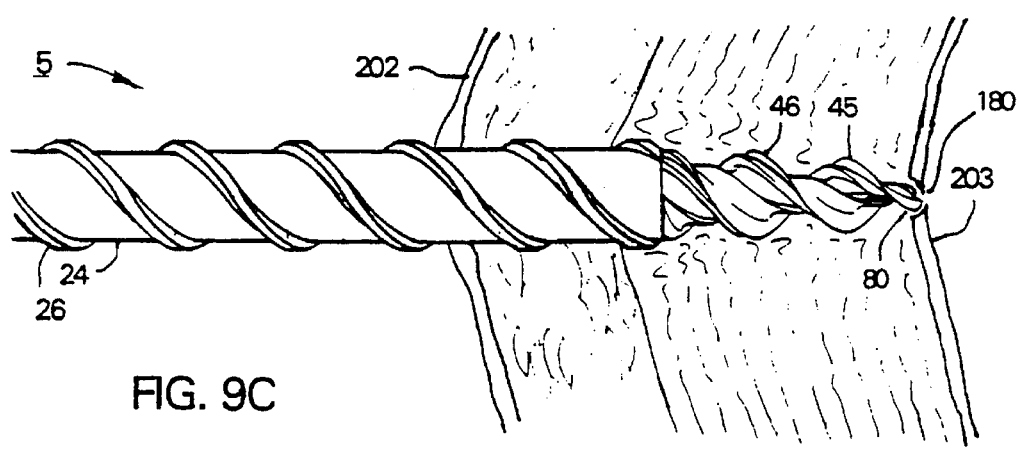

FIG. 9C illustrates helix 10 after having been advanced through tissue with the leading edge 80 of blade 40 beginning to incise an arc in the inner membrane 203 of the abdominal wall. As shown an instant later in FIG. 9D, the relaxation of counterforce exerted by tissue against the probe tip 180 permits the probe 100 to project outward (distally). This action causes the trip mechanism to disengage the latch and disarm helix 10, thus preventing any sharp blade edge from entering into the abdominal cavity.

Figure 9D:
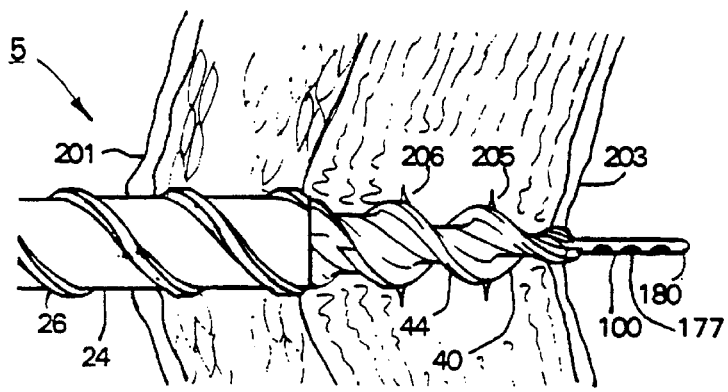
Figure 9E:
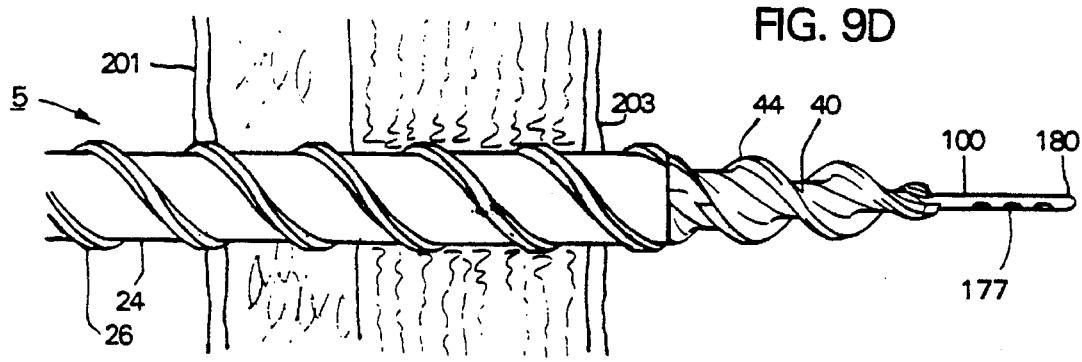
Figure 9F:
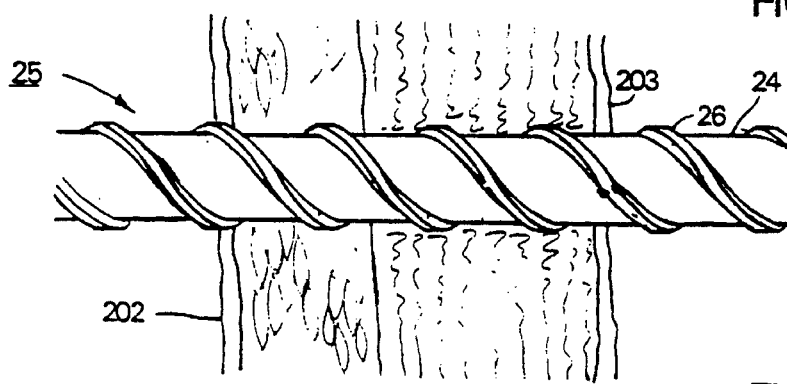

With instrument 5 again in the non-incising position as shown in FIG. 9D, the surgeon than can helically advance the instrument into the abdominal cavity. As shown in FIGS. 9D–9E, helical threads 26 of cannula 24 cooperate with helix 10 to grip tissue surrounding the incised pathway to drive the instrument inwardly. Finally, as shown in FIG. 9F, the heliscopic cutter 5 may be withdrawn from the cannula assembly 25 thus leaving cannula 24 within the incised pathway to provide access to the interior of the body.

The specific internal structure of the heliscopic cutter 5 now will be described with reference to FIG. 10A, which is a longitudinal sectional view thereof. It is possible to describe the manner in which the latch mechanism maintains helix 10 in an armed or incising position and the manner in the latch is tripped to transform helix 10 to the non-incising position.

Variform helix 10 is coupled to distal end 22 of introducer sleeve 20. More particularly, reduced diameter shank 102 of blade 40 is fixed in bore 110 of introducer sleeve 20, thus allowing shield 44 to travel helically around axis 11 and along helicoidal interfaces, "M" and "N" Reduced diameter portion 105 of shield 44 is dimensioned to move freely in bore 110 of introducer sleeve 20. Helix sleeve 120 is dimensioned for axial reciprocation and rotational movement within bore 110 of sleeve 20 and is coupled to shield member 44 to allow a slip fit in rotation. An annular recess 128 in axial bore 130 that extends through helix sleeve 120 is dimensioned to receive flange 132 in the proximal end of shield 44. The helix sleeve 120 is urged to its proximalmost or rest position by spring 135 compressed between flange 136 of helix sleeve 120 and stop plate 138, which in turn positions helix 10 in the non-incising position.

It must be noted that outward (distal) movement of sleeve 120 will cause smooth axial and angular (i.e., helical) movement of shield 44 relative to blade 40 along helicoidal interfaces "M" and "N" only when constant spiral lead (pitch) 33 of interfaces "M" and "N" is approximately 0.500" or greater. Variform helixes with lesser spiral leads, as described above, fall within the scope of the present invention and require a helix sleeve that is actuated at least in part by a torsion spring, rather than a compression spring only, to both rotationally and angularly actuate shield 44 relative to blade 40.

Referring still to FIG. 10A, heliscopic cutter 5 incorporates a latch mechanism, the function of which was described briefly above. In detail, the latch retains shield 44 in a proximal armed position when latch arms 140 with hooks 142 override and engage annular notch 144 in the proximal end of helix sleeve 120 as the helix sleeve slides proximally over trigger housing 148. The pivotable latch arms 140 are made of spring-like molded resilient plastic which urges hooks 142 radially inward to engage notch 144. The hooks 142 have cam surface 145 to allow it to override shoulder 146 adjacent to notch 144 as helix sleeve 120 is pushed inward (proximally).

In addition, a trip mechanism to disengage the latch includes a resilient plastic trigger 150 that is slidably disposed in axial trigger chamber 152 within trigger housing 148. The plastic trigger 150, shown generally in FIG. 10A and more specifically in axionometric view in FIG. 11, has circumferentially spaced flexible spring arms 155 with annular tab 156 that is dimensioned to contact cam surface 145 incorporated into latch arms 140 that extend into trigger chamber 152. Trigger 150 is limited in its axial travel in trigger chamber 152 by proximal and distal ends of the trigger chamber. An axial bore 158 extends through the distal end of trigger 150 and is radially sized so as to permit the trigger to slide to and fro over a section of probe 100 between stop collar 160 and trip collar 165.

Reciprocating probe 100 actuates the trip mechanism for disengaging the latch. Probe 100, with central bore 166, is urged in an outward (distal) direction to its projected position by spring 170. Probe 100 extends through axial bore 130 in helix sleeve and aligned bore 32 through blade 40 and shield 44. The probe extends beyond the distal end of helix 10 extension distance "E" ranging from e.g. 0.250" to 1.00" The distal region of the probe is provided with a plurality of apertures 177 and terminates in a closed rounded tip 180 for reasons described below.

The outward (distal) travel of probe 100 is limited by stop collar 160 abutting stop 182. The stop collar 160 is fixed to probe 100 and radially sized to slide longitudinally in collar bore 184. Reciprocating probe 100 further includes a fixed trip collar 165. A counterbore 185 in trigger 150 is provided that is radially sized to permit trip collar 165 to seat therein.

Referring still to FIG. 10A, an arming mechanism is included within handle assembly 15 for arming helix 10. Arming sleeve 190 is slidably disposed in bore 192 in handle 15 and spring 195 is captured between stop plate 138 and the proximal face of sleeve 190 and urges the arming sleeve 190 in the distal direction. Arming sleeve 190 includes diametrically opposed finger grips 196 that project radially outward through slots 197 in handle 15. The arming sleeve 190 is limited in distal movement by end plate 198 that is secured in the distal end of bore 192, with introducer sleeve 20 fixed into end plate 198. Arming sleeve 190 has central bore 199 along its axis 11 with inward-projecting flange 200 that engages outward-projecting flange 136 of helix sleeve 120 for arming the instrument.

In operation, the above-described latch and trip mechanisms in cooperation with helix sleeve 120 mechanize the variform helix and provide the sequential positions of the helix shown in FIGS. 9A–9D. In particular, FIGS. 10A–10D (which correspond in sequence to FIGS. 9A–9D) illustrate the sequence of movements of the internal elements of the heliscopic cutter from arming the instrument through incising a pathway in an abdominal wall.

Before the instrument is used, the heliscopic cutter 5 is assembled with cannula assembly 25 as shown in FIG. 1, at which stage the variform helix remains in its non-incising position. Next, referring to FIG. 10A, the surgeon grasps handle 15 with one hand and utilizes the thumb and index finger (of either hand) to slide the finger grips 196 proximally overcoming the counterforce exerted by spring 195. The arming flange 200 contacts helix sleeve flange 136 and thus pushes helix sleeve 120 proximally, which in turn moves shield 44 axially and angularly (i.e., helically and slightly proximally). The inward travel of helix sleeve 120 causes shoulder 146 to push on the angled edge of hooks 142 which bends latch arms 140 outward slightly until hooks 142 rebound to engage annular notch 144 in the helix sleeve, thus arming the instrument.

In the armed or incising position, as shown in FIG. 10A, the instrument is prepared to incise a pathway in tissue. Holding the instrument in one hand, the surgeon pushes the distal tip 180 of the probe into small incision 201 (see also FIG. 9B). As shown in FIG. 10B, the counterforce exerted by tissue causes the probe to be urged inward (proximally) overcoming the resistance of spring 170. During positioning of the distal end of helix 10 within the incision, probe 100 may move in and out somewhat providing a "retraction float" to facilitate the initial positioning of the cutting device. In other words, the probe is required to retract a set distance, for example from 50% to 90% of the extension distance "E", before annular tab 156 of trigger 150 contacts cam surfaces 145 of latch arms 140 as depicted in FIG. 10B. The spring constant of the spring arms 155 is less than the spring constant of latch arms 140 thus allowing spring arms 155 to bend inwardly as tab 156 passes under cam surfaces 145, which then prepares the trip mechanism to disengage the latch.

Figure 10C:
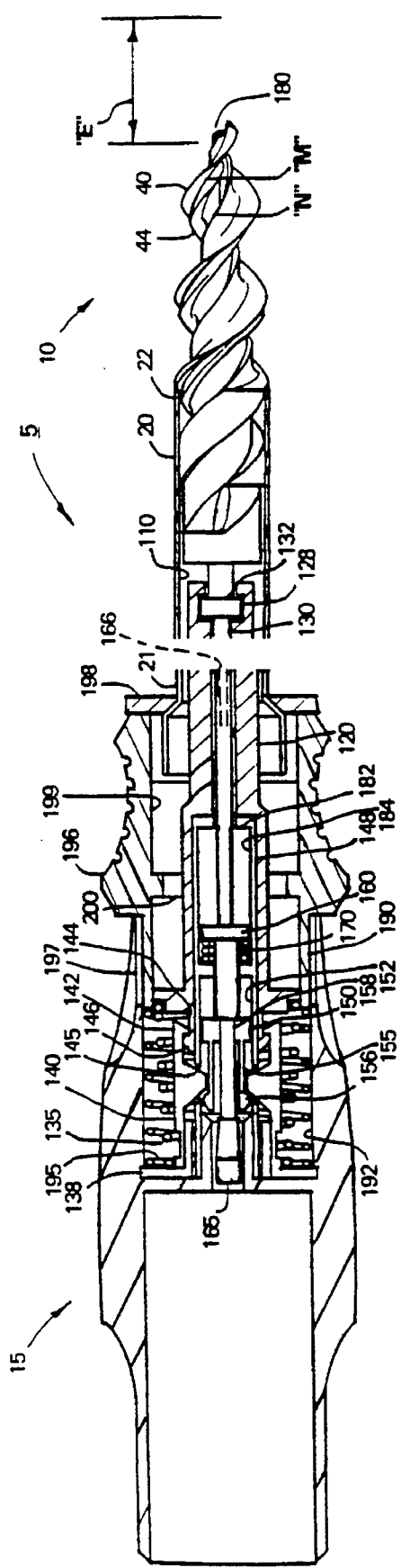

Of particular interest to the present invention, referring to FIG. 10C, the surgeon may relax rotational and axial pressure on the instrument while incising a pathway without concern that the abdominal wall will repel the instrument tip as is typical with puncturing trocars. The helix is held in place within the tissue by the screw-like shape (i.e., helical channel 70 and protrusions 35, 36) that serve to anchor the helix in tissue and counterbalance the repelling forces. In this regard, the radial depth of channel 70 as well as the angle of proximal channel face 76 are dimensioned to adequately grip tissue. With the helix thus anchored in tissue, the surgeon may lift the instrument while rotating it to lift the abdominal wall away from internal organs as an added safety precaution (see FIGS. 9C–9D). This is to be contrasted with puncturing trocars, in which powerful axial forces are necessary to make a puncture inwardly thus pushing the abdominal wall inward toward internal organs.

Of particular interest to the present invention, the trip mechanism enjoys "projection float" as the probe is urged outward under the influence of spring 170. Referring to FIG. 10C, the trigger 150 may "float" within trigger chamber 152 along a space between trip collar 165 and stop collar 160. Such projection float allows the surgeon to unscrew the instrument slightly from the tissue, for example to redirect the instrument, allowing the probe to project into the vacated pathway without the trip mechanism being triggered to disarm the helix. Probe 100 may extend a set distance ranging from 75% to 95% of extension distance "E" before actuating the trip mechanism.

Figure 10D:
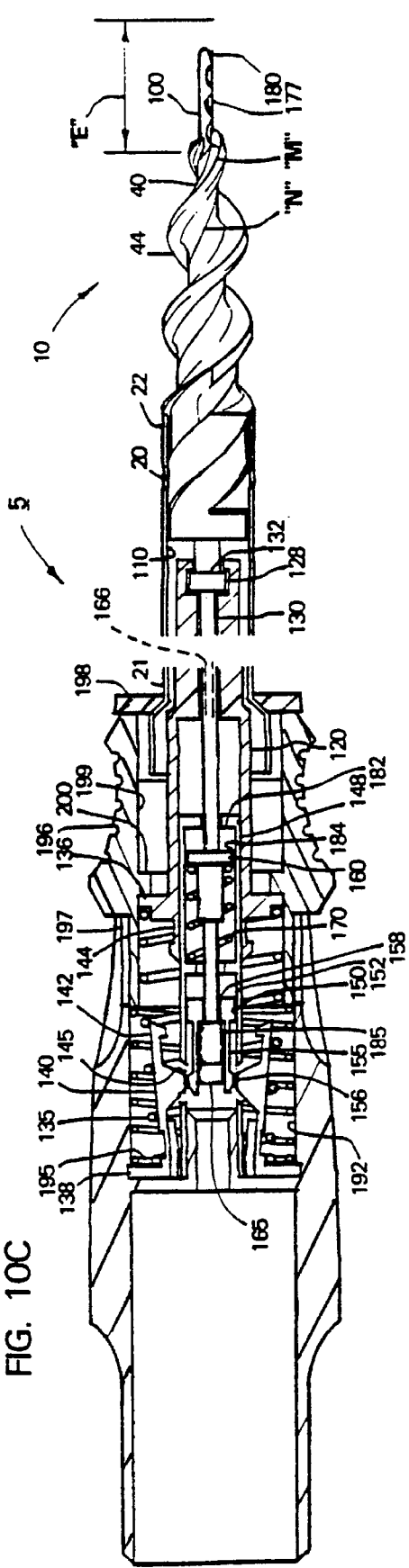
Figures 16, 17, 18:
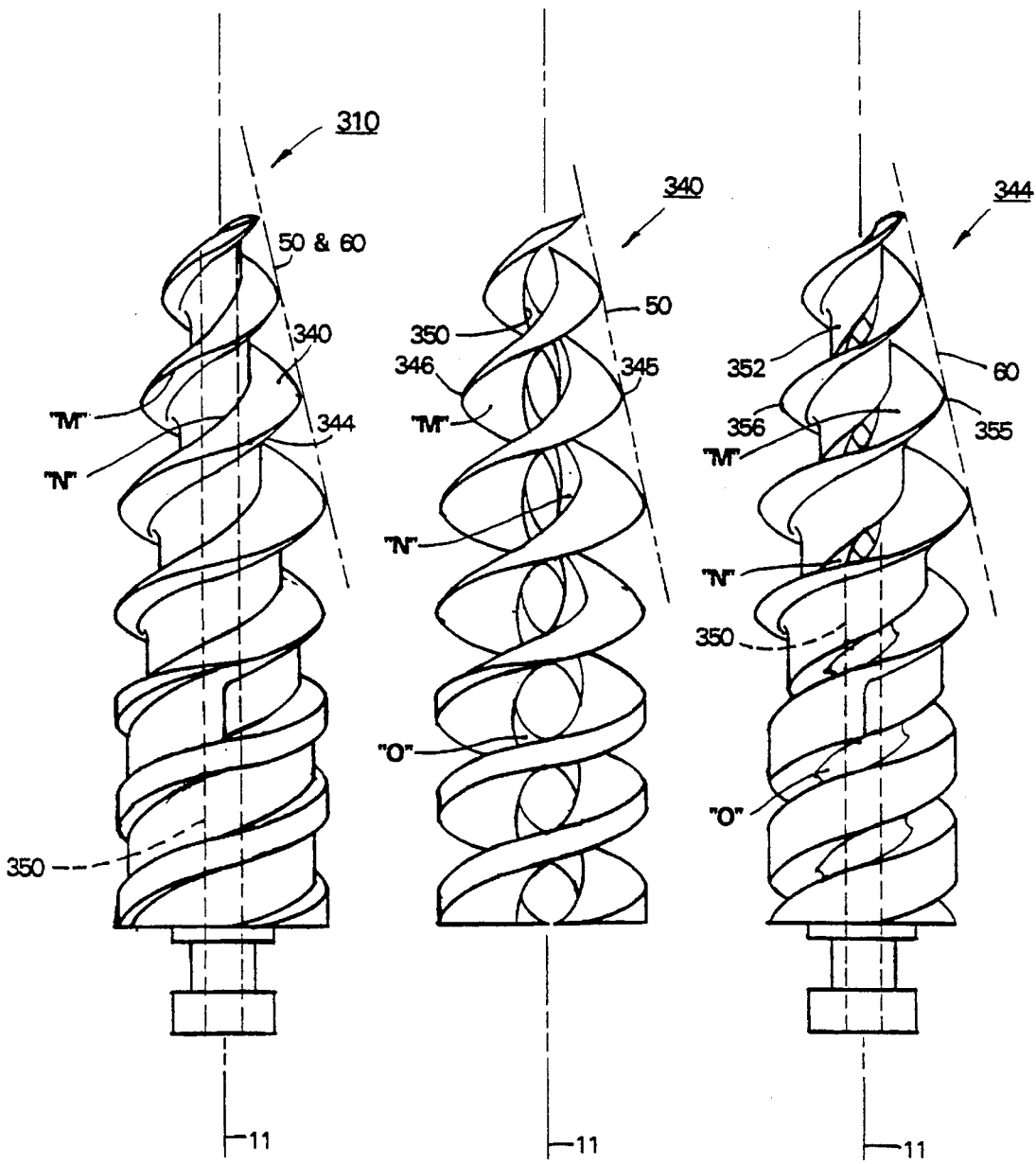
FIG. 16 is an elevational view of a third embodiment of variform helix in a first (non-incising) position.
FIG. 17 is an elevational view of a de-mated first or blade member of the third embodiment of variform helix of FIG. 16.
FIG. 18 is an elevational view of a de-mated second or shield member of the third embodiment of variform helix of FIG. 16.

Referring next to FIG. 10D and FIG. 9D, as the leading edge 80 of the blade incises an arc in the inner membrane of the abdominal wall, the resulting relaxation of counterforce against tip 180 of probe 100 causes the probe to move distally under the influence of spring 170. Trip collar 165 then seats itself in counterbore 185 in trigger 150 thus preventing spring arms 155 from bending radially inward. In this regard, as shown in FIG. 10D, further distal movement of probe 100 then causes annular tab 156 on trigger 150 to contact cam surfaces 145 and push the latch arms 140 radially outward to release hooks 142 from engagement with annular notch 144. Such disengagement of the latch mechanism permits spring 135 to drive helix sleeve 120 distally which, in turn, helically advances shield 44 relative to blade 40 along helicoidal interfaces "M" and "N" to transform helix 10 to the non-incising position. Having detailed the sequence of movements of the internal latch and trip mechanisms, other structures incorporated into the instrument are hereafter described.

Of particular interest to the present invention is the manner in which leading blade edge 80 cooperates with probe 100 in incising a pathway through tissue. As shown in FIGS. 9C and 10C, the most inward (proximal) travel of probe 100 allows probe tip 180 to seat itself well inward from leading blade edge 80. As leading edge 80 is helically advanced through tissue, the distalmost blade tip and edge seemingly would "corkscrew" slightly through tissue around the diameter of probe 100 which is on the centerline of the incised path. In practice, the pliability of the tissue allows the leading blade edge 80 to "induce" a centerline incision in advance of probe tip 100 thus insuring that probe tip 180 will not cause drag and will follow leading edge 80 through tissue. In this regard, the lagging blade edge 82 is adapted to follow well behind probe tip 180 to avoid any "coring" effect, that is, incising around the diameter of probe 100.

Of particular interest to the present invention is the manner is which the incised pathway is further expanded to accommodate cannula 25, referring to FIGS. 9C–9D. At the stage of the incising sequence shown in FIG. 9C, it will be noted that the pathway is helically incised entirely through the abdominal wall. The incised pathway was accomplished with a blade periphery 50 that was exposed distance "H" or only slightly beyond the lands periphery 60. In other words, the helical blade edges incised only very shallow helical blade tracks, 205 and 206 in tissue around the axis 11 of the pathway. Helical blade tracks 205 and 206 are indicated in FIG. 9D in somewhat exaggerated depth. It will be noted that such blade tracks 205 and 206 are "non-intersecting" each having depth "H" (blade exposure) and are best illustrated in FIG. 12A, an axionometric line drawing of the tracks around pathway axis 11 with instrumentation removed from the pathway. With regard to expanding the incised pathway to accommodate a cannula, the transverse sectional dimension of the path is expanded by "stretching" tissue circumferentially around axis 11 by advancing the increasing transverse sectional dimension of the helix into the pathway. In other words, the tissue is "displaced" generally radially outward from the pathway axis 11 to finally provide a pathway diameter equal to the dimension of cannula 24. Yet the deepest incision in tissue is a small fraction ("H") of transverse dimension "S" of the pathway as depicted in FIG. 12A. This aspect of the invention is to be contrasted with the cuts of a puncturing trocar, as shown in FIG. 12B, in which the sharp edges of the trocar tip make "intersecting" longitudinal incisions 207, 208 and 209 resulting in incision depth T1 plus T2 that generally spans the transverse dimension "S" of the pathway. The shallow helical blade tracks 205 and 206 allow for rapid healing of tissue.

Of particular interest to the present invention is channel 70 incorporated into the variform helix which is designed to displace tissue (expand the pathway) by forces that are applied perpendicularly to axis 11 of the pathway. The inner face 75 of the channel is parallel to axis 11 of the instrument, and therefore the increasing transverse dimension of the channel inner face 75 displaces tissue perpendicularly outward relative to the axial travel of the helix as the helix rotates (see FIGS. 4, 7 and 10D). The angular rise "Q" of inner face 75 of the channel displaces tissue radially outwardly in a gradual manner, depending entirely on the degree of angular rise "Q". Such axis-perpendicular "displacement" of tissue is to be contrasted with conventional trocars that puncture and tear tissue with a steeply angled pyramidal tip that generally displaces tissue by forcing it inwardly, thus creating additional longitudinal forces on the abdominal wall and internal organs.

A second embodiment of variform helix 210 is shown in FIGS. 13–15 in which like reference numerals refer to elements common to the first-described embodiment of FIGS. 4–8. Helix 210 differs from the first-described embodiment in that the helicoidal interfaces, "M" and "N", along which blade 240 and shield 244 helically mate do not extend inward to axial bore 245 in the helix. Rather, there is an inner surface or helical interface "O" that contours between the generally helicoidal interfaces "M" and "N". Thus, the cooperating plastic shield member 244 is dimensioned to helically travel in the groove circumscribed by the three helical interfaces, "M", "N" and "O". Plastic shield 244 may be made of a slippery material such as Teflon to reduce friction with tissue. It is feasible to fabricate blade 240 of stainless steel with a computer numeric controlled multi-axis grinding center, for example a seven-axis ANCA model MG-7 available from ANCA U.S.A., Inc. of Novi, Mich. Alternatively, blade 240 may be fabricated by molding a plastic. Helix 210 may be coupled to sleeve 10 of instrument 5 to function as previously described.

Figure 19:
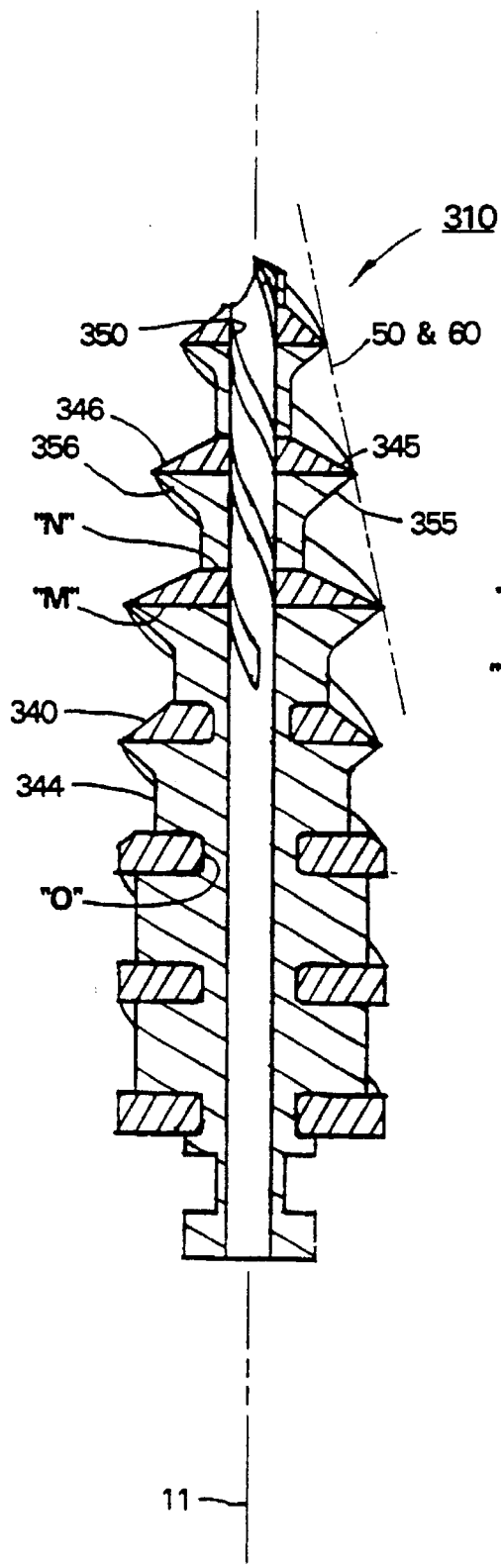
FIG. 19 is a sectional view of the third embodiment of the variform helix of FIG. 16 taken along line 19—19 of FIG. 16.
Figure 20:
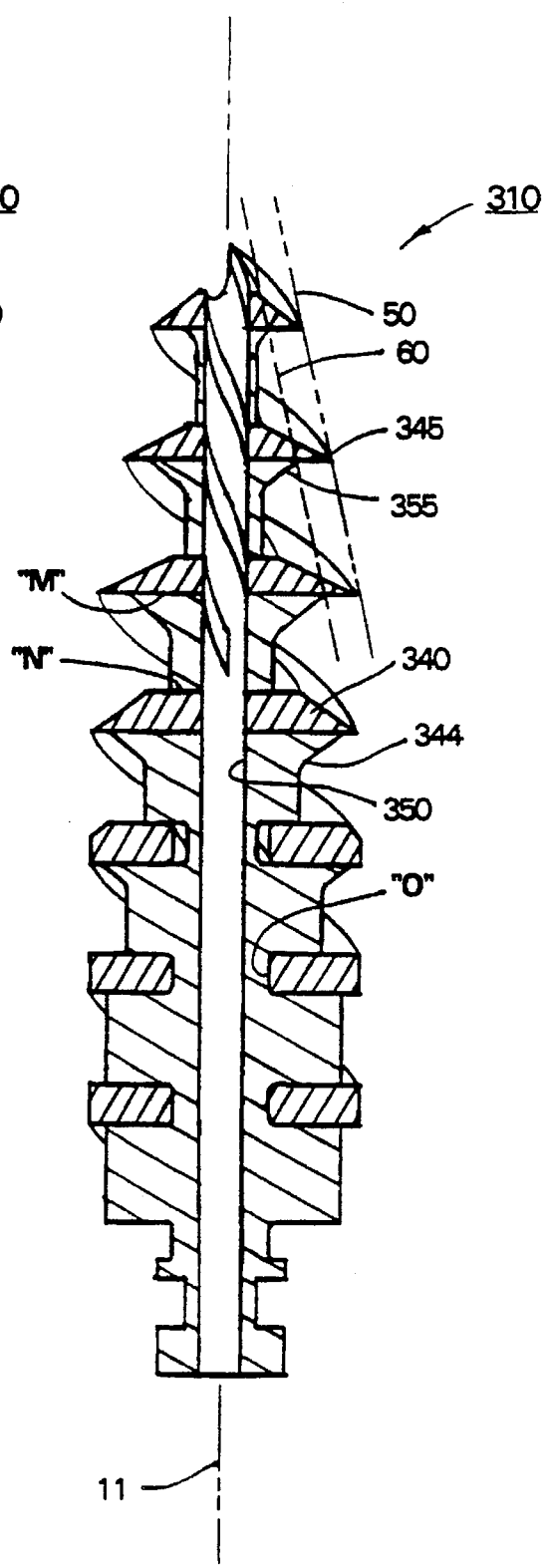
FIG. 20 is a sectional view of the variform helix of FIG. 16 in a second (incising) position.

A third embodiment of variform helix 310 is shown in FIGS. 16–20. Variform helix 310 differs in that the helical interfaces, "M" and "N" and "0" along which blade 340 and shield 344 helically mate circumscribe a thin-section blade that extends inward to axial bore 350 only in the distal region 352 of helix 310 (see FIG. 18). As in previous embodiments, the outer blade edges of the dual-lead blade, 345 and 346, are sharp and generally capable of incising tissue (see FIG. 17). However, in this embodiment, the outer edge of the helical protrusion of shield member 344 also exhibits somewhat sharp helical edges, 355 and 356 (see FIG. 18). As shown in FIGS. 19–20, it is the combined angles of an outermost blade and shield edges, for example edges 345 and 355 as shown in FIG. 20, that make helix 310 substantially capable of incising tissue in the incising position. FIG. 20 shows a sectional view of helix 310 in the incising position with blade periphery 50 exposed radially outward from shield periphery 60. FIG. 19 shows helix 310 in the non-incising position in which it is less capable or incapable of incising tissue. Blade member 340 is adapted to be fixed in sleeve 20 (not shown) as in the first embodiment.

Figure 21:
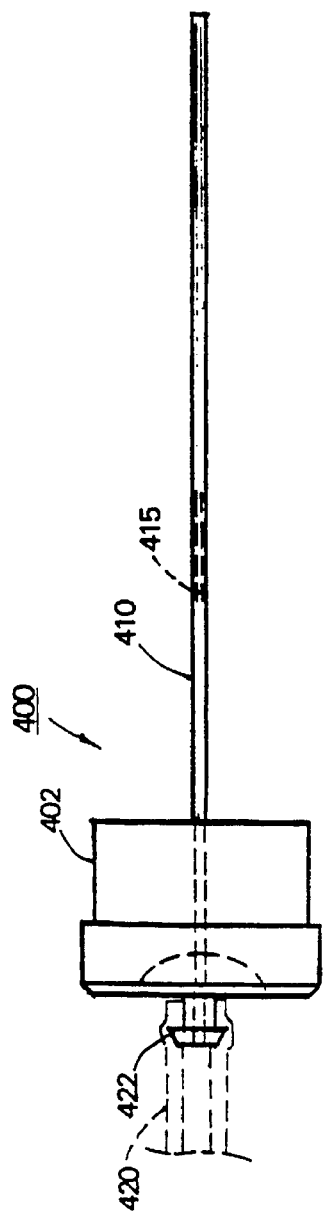
FIG. 21 is an elevational view of a component of a heliscopic cutter.
Figure 22:
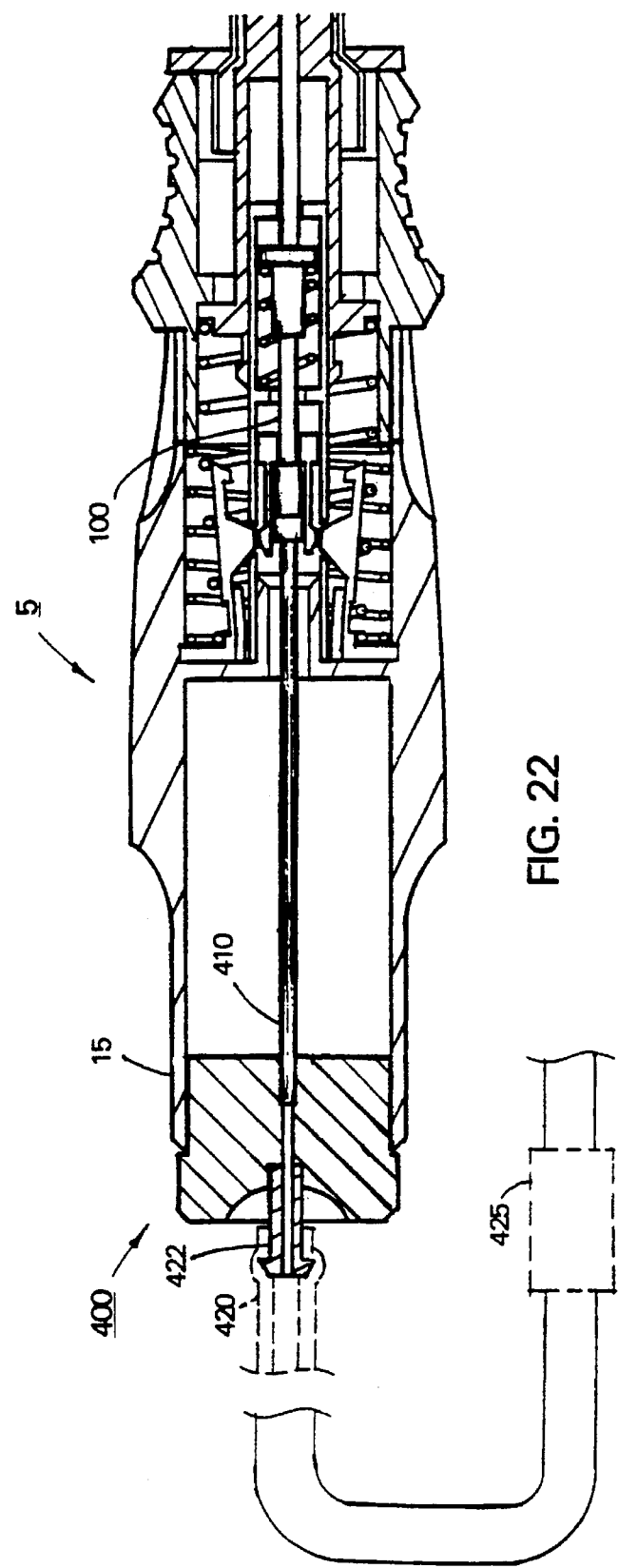
FIG. 22 is an elevational view of the component of FIG. 21 fitted to a heliscopic cutter.

The heliscopic cutter may also be provided with an "automatic" insufflation mechanism. Referring to FIGS. 21–22, plastic $CO_2$ adapter 400 has a cylindrical portion 402 that is dimensioned to press fit into the proximal end of handle 15. Rigid supply tube 410 with bore 415 is adapted to extend through handle 15 and into the open proximal end of bore 166 in reciprocating probe 100 (see FIG. 22). A flexible $CO_2$ supply hose 420 is connected to Luer-type fitting 422 in the proximal end of $CO_2$ adapter 400. As the surgeon advances the variform helix of instrument 5 into the abdominal wall, an assistant opens a valve allowing $CO_2$ to flow through hose 420 at a "low flow" rate and thereafter through bore 415 of tube 410 and bore 166 of probe 100. The external insufflation source contains flow sensor 425 that increases $CO_2$ flow to a "high flow" rate from the "low flow" rate after sensor 425 senses that $CO_2$ is flowing at the low flow rate. While the helix is embedded in tissue as the pathway is being incised, apertures 177 in probe 100 are covered since the probe is within bore 32 in the helix thus restricting $CO_2$ flow (see FIG. 9C). As probe 100 projects outward (distally) into an anatomic cavity as shown in FIG. 9D, $CO_2$ flows under the low flow rate through probe apertures 177 into the cavity and instantly thereafter sensor 425 triggers $CO_2$ flow at the high flow rate to insufflate the abdominal cavity in from 1 to 2 minutes thus providing an insufflated workspace. This aspect of the invention is to be contrasted with current practice that requires 5 to 10 minutes to first insufflate the abdominal cavity through a small diameter Verress needle, only after which trocars are utilized to place cannulas in the abdominal wall.

Figure 23A:
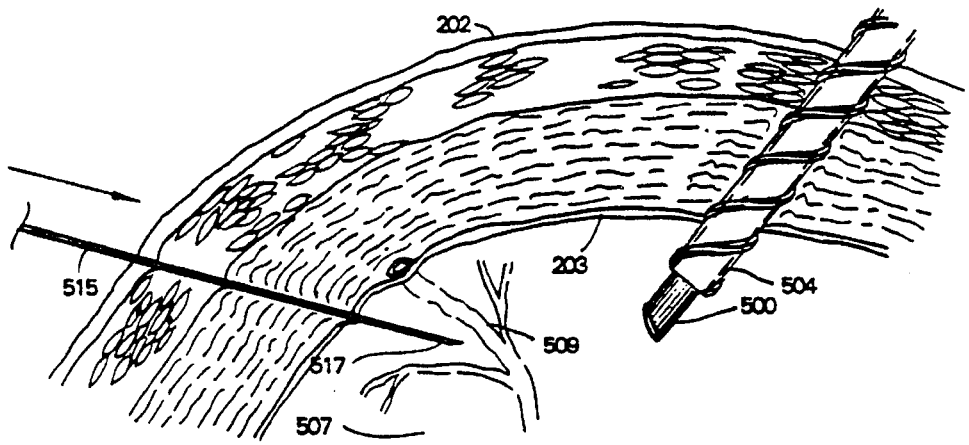
FIGS. 23A–23B are sectional illustrations showing the manner in which a method of the present invention is practiced utilizing the instrument of FIG. 1.
Figure 23B:
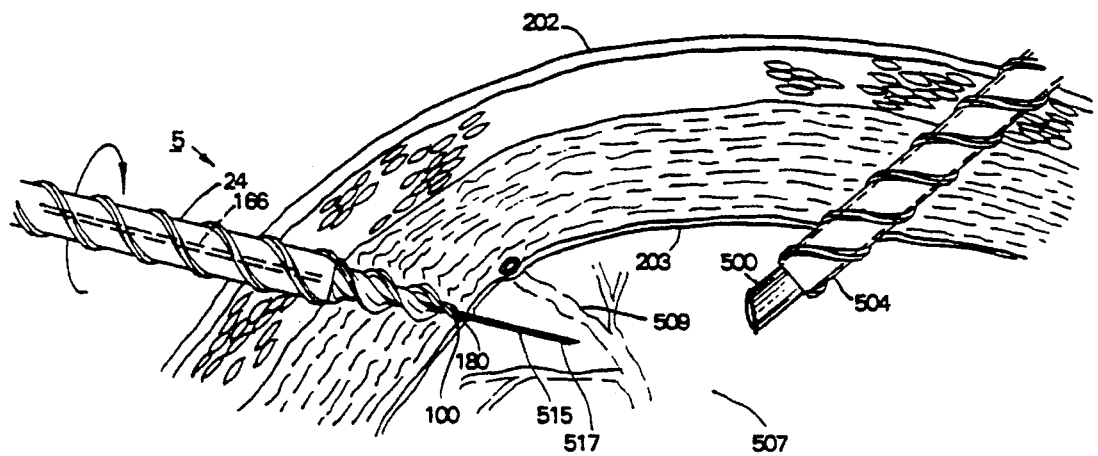

FIGS. 23A–23B depict an alternative method of utilizing instrument 5 with any embodiment of heliscopic cutter. It often is desirable to make an incision for a cannula in a precise location, for example, to avoid cutting sensitive anatomic structures in the body wall overlying an anatomic cavity. In FIG. 23A, endoscope 500 is disposed in cannula 504 within abdominal cavity 507. The abdominal wall has outer skin 202 and peritoneum 203 lining abdominal cavity 507. The surgeon can view artery 509 through endoscope 500 just beneath peritoneum 203. If the surgeon utilized a conventional puncturing trocar (not shown), it would be difficult to make an incision in the region of artery 509 without risk of injury to the artery due to the axial forces required to force a large-diameter trocar tip through the abdominal wall. However, it is relatively easy to utilize small diameter guide needle 515 to penetrate the abdominal wall in a precise location while viewing through endoscope 500. For example, the penetration of an elongate 18 mm. needle (not limiting) causes little pressure on the body wall. Thereafter, as shown in FIG. 23B, guide needle 515 is used as a guide over which instrument 5 is advanced through the abdominal wall. Instrument 5 differs from the above described embodiments in that tip 180 of reciprocating probe 100 has a center-line aperture communicating with bore 166 of the probe to allow needle 515 to pass entirely through the instrument.

Figure 24A:
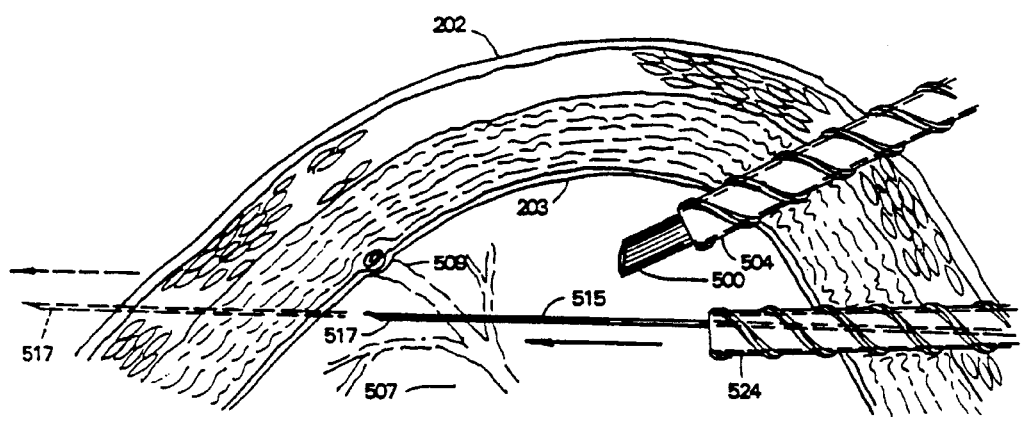
FIGS. 24A–24B are sectional illustrations showing the manner in which another method of the present invention is practiced utilizing the instrument of FIG. 1.
Figure 24B:
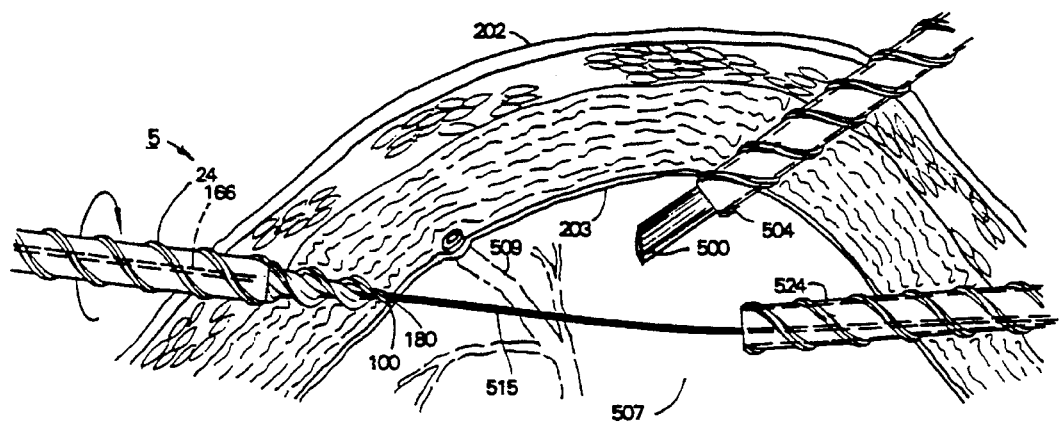

FIGS. 24A–24B illustrate an important variation of the method of utilizing instrument 5 to safely make an incision in a precise location to avoid injury to a sensitive anatomic structure in an anatomic wall. Cannulas 504 and 524 are disposed within the abdominal wall and the surgeon may view artery 509 under peritoneum 203 through endoscope 500. The surgeon then introduces guide needle 515 through cannula 524 into the insufflated abdominal cavity 507. FIG. 24A shows the tip of needle 515 advanced to a precise location clear of artery 509. Then, under endoscopic vision, the surgeon easily may push the needle from the inside of cavity 507 to the exterior of the body thus safely avoiding injury to artery 509 (see phantom view in FIG. 24A). Such an "inside-out" incision avoids application of any inwardly-directed forces. Referring to FIG. 24B, the surgeon then places instrument 5 over the tip of needle 515 exposed outside the body and uses guide needle 515 as a guide to advance the heliscopic cutter 5 together with cannula 24 into cavity 507. Thereafter, guide needle 515 may be withdrawn either through cannula 24 or cannula 524. It should be noted that guide needle 515 may be introduced along with an endoscope through a single cannula to make an inside-out incision under endoscopic vision, for example utilizing a 5 mm. endoscope and a guide needle within a 10 mm. cannula.

Figures 25, 26:
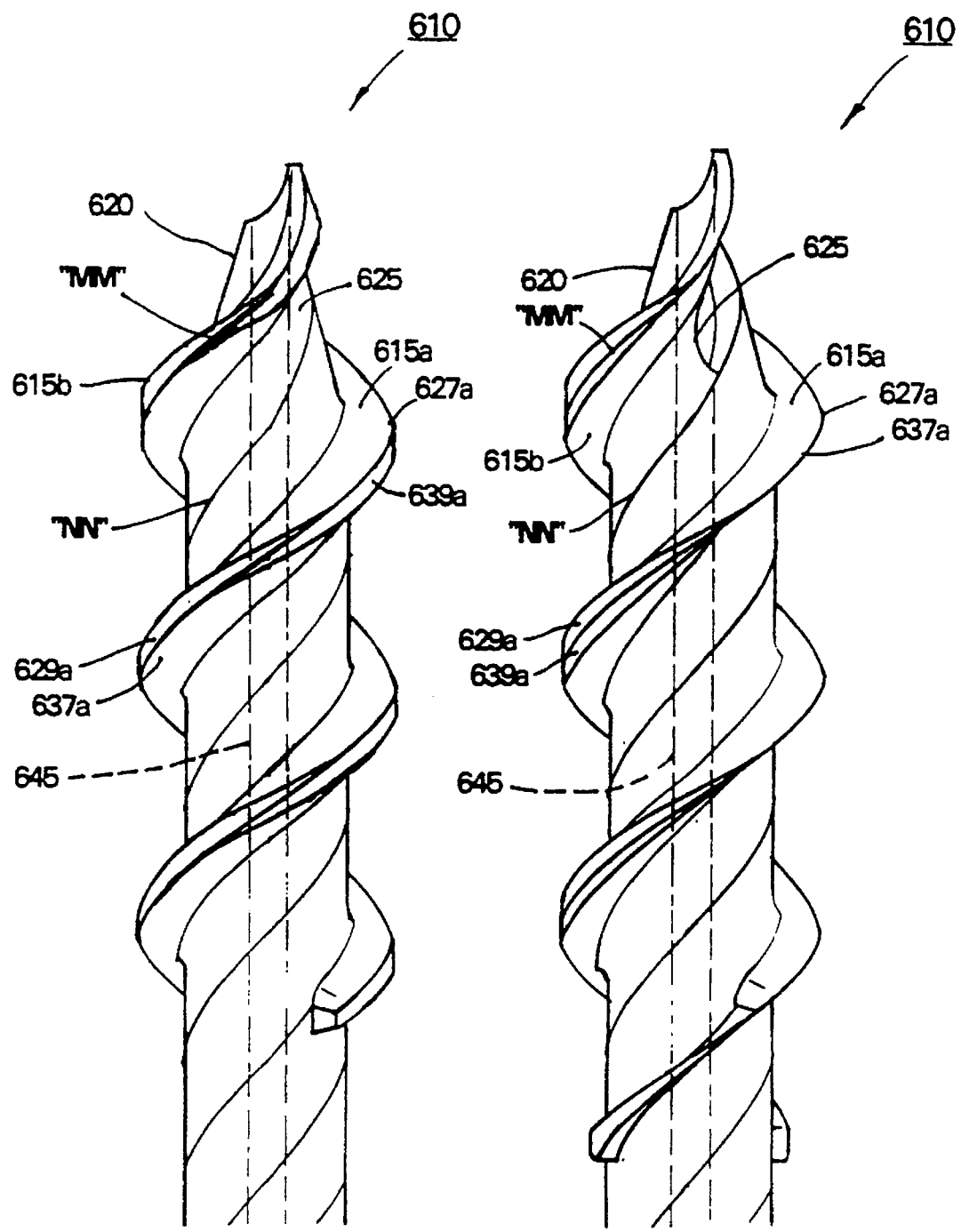
FIG. 25 is an elevational view of a fourth embodiment of variform helix in a non-incising position.
FIG. 26 is an elevational view of a variform helix of FIG. 25 in an incising position.

In the above-described embodiments of variform helixes, the helical protrusion is transformed between sharp-edged and dull-edged positions by moving tapered peripheries of helical mating parts in and out of registration. It also is possible to provide a helical protrusion that is transformable between a sharp-edged incising position and a dull-edged non-incising position without utilizing tapered peripheries of mating parts. Referring to FIGS. 25–26, partly cylindrical variform helix 610 includes first member 620 and second member 625 that mate along helical interfaces "MM" and "NN". As can be seen in FIG. 25, the double-lead helical protrusions 615a and 615b are jointly defined by the helical edges of the first and second members, 620 and 625, respectively. Interface "MM" splits the outer edge of the helical protrusions. The helical edges of members 620 and 625 are asymmetrical in cross-section relative to interface "MM" as they wrap around the periphery of helix 610. For example referring to FIG. 25, the helical outer edge of first member 620 along protrusion 615a varies from sharp-edged portion 627a to dull-edged portion 629a along the spiral of the helical protrusion. Likewise, the helical edge of second member 625 along helical protrusion 615a also varies from sharp-edged portion 637a to dull-edged portion 639a. In FIG. 25, the edges vary from sharp to dull over a radial angle of 90° (not limiting).

In FIG. 25, helix 610 is shown in the non-incising position in which the sharp-edged portion 627a of first member 620 is adjacent along interface "MM" to dull-edged portion 639a of second member. At the same time, dull-edged portion 629a of first member 620 is adjacent along interface "MM" to sharp-edged portion 637a of second member 625. The dull-edged portions of each member, 620 and 625, shield the sharp-edged portions the members thus providing a helical periphery that is not capable of incising tissue.

Referring to FIG. 26, second member 625 is rotated relative to first member 620 to provide an incising position. In the incising position, helix 610 has sharp-edged portion 627a of first member 620 adjacent along interface "MM" to the sharp-edged portion 637a of second member 625. At the same time, dull-edged portion 629a of first member 620 is adjacent along interface "MM" to dull-edged portion 639a of second member 625. Thus, it can be seen that relative helical movement of first member 620 and second member 625 may cause a helical periphery that has alternating sharp-edged portions and dull-edged portions.

Asymmetrical helically mating protrusions are useful for small diameter incising instruments in which the tapered section is short. Such asymmetrical helical protrusions are particularly useful for cylindrical-shaped instruments in which it is desirable to have a helical edge for gripping tissue as well as for incising tissue around a pathway. In such a helix, the first and second members may be helically actuated relative to one another by a reciprocating probe as in the first-described embodiment. Alternatively, there may be provided a manual release for a latch mechanism that maintains helix 610 in the incising position. The use of such asymmetrical helical protrusions also is useful for helixes with tapered peripheries in order to move the helix between incising and non-incising positions with little angular movement.

Although specific embodiments of the present invention have been described above in detail, it will be understood that this description is for purposes of illustration. As will be appreciated by one skilled in the art, the device in accordance with the present invention may have a blade that is movable between an incising and non-incising position relative to a stationary shield. As a further example, the mating interfaces between the blade and shield that are herein described as helicoidal interfaces and exhibit a flat surface viewed in longitudinal section, may exhibit any curvilinear sectional shape that allows for the blade periphery to be exposed outside the lands' periphery. As a further example, the trip mechanism for disengaging the latch to transform the helix to the non-incising position from the incising position may be the distal helical movement of the shield member due to a relaxation of tissue drag on the shield as the blade member penetrates into an anatomic cavity.

As a further example, a blade member made from a thin flexible strip such as stainless steel may be disposed within a thin helicoidal-configured slot or groove centered within the lands of a variform helix. As a further example, a helical blade member made from a thin flexible strip such as stainless steel may be deformed through relative rotation of the proximal and distal ends thereof so as to develop an expanded tapered blade periphery that is exposed beyond the fixed tapered shield periphery of a rigid shield member to provide helical blade edge exposure. As a further example, a tapered shield member made from a resilient plastic may be deformed through relative rotation of the proximal and distal ends thereof so as to develop a reduced-taper shield periphery that falls inside the fixed blade periphery of a rigid blade member to provide helical blade edge exposure.

As a further example, a pressurized gas canister may be carried within the handle of the heliscopic cutter to provide an internal insufflation source which is actuated by the probe as it projects into an anatomic cavity.

Various modifications of equivalent structures corresponding to the disclosed aspects of the above-described embodiments may be made by those skilled in the art.

What is claimed is:

1. A surgical instrument, comprising:

a longitudinally-extending sleeve; and an incising assembly carried at a distal end of the sleeve, and comprising a blade member having at least one sharp helical blade edge capable of incising tissue and a cooperating slidable mating and interfitting shield member having an outer periphery not capable of incising tissue, the incising assembly thereby allowing relative helical movement between a non-incising and an incising position of the blade and shield members, wherein in the non-incising position the helical blade edge is not exposed, thereby to prevent incising of tissue by the blade edge and in the incising position the helical blade edge is exposed, thereby to allow incising of tissue by the blade edge;

a blade-exposing mechanism coupled to the blade and shield members of the incising assembly for exposing the blade member in the incising position; and a shielding mechanism coupled to the blade and shield member of the incising assembly, thereby to move the incising assembly to the non-incising position from the incising position.

2. A surgical instrument, comprising:

an incising assembly having a longitudinal axis and having a helically protruding edge and further comprising a first member and a second member that interfit and slidably mate along helical mating interfaces around the axis and jointly define the helically protruding edge and an actuating mechanism coupled to the first and second members, thereby to actuate relative movement between the first and second members, the incising assembly thereby allowing relative helical travel of the first and second members along said mating interfaces to provide non-incising and incising positions of the first and second members, wherein in the non-incising position the helical protruding edge is not capable of incising tissue and in the incising position the helical protruding edge is capable of incising tissue.

3. The instrument of claim 2, wherein outer peripheries of the first and second members each have a decreasing transverse cross-section in the distal direction along the longitudinal axis.

4. The instrument of claim 2, wherein the first member has a sharp helically protruding edge capable of incising tissue and the second member has a dull helically protruding edge not capable of incising tissue.

5. The instrument of claim 2, wherein the first member has a helically protruding edge with alternating sharp edge portions capable of incising tissue and dull edge portions not capable of incising tissue and the second member has a helically protruding edge with alternating sharp edge portions capable of incising tissue and dull edge portions not capable of incising tissue cooperating with respectively the sharp and dull edge portions of the first member.

6. The instrument of claim 2, wherein the first and second members each have a helical protruding edge capable of incising tissue, wherein said helically protruding edges when adjacent to each other provide a helically protrusion that is not capable of incising tissue.

7. The instrument of claim 2, wherein said helically-protruding edge in the non-incising position is adapted for threadably engaging tissue.

8. The instrument of claim 2, wherein the incising assembly has a plurality of helical protruding edges and the first and second members helically mate along a plurality of helical mating interfaces, the plurality of helically protruding edges being capable of transformation between the non-incising and incising positions.

9. The instrument of claim 2, further comprising:
   an introducer sleeve carrying said incising assembly at a distal end thereof;
   a maintaining mechanism operatively connected to said incising assembly for releasably maintaining the incising assembly in the incising position;
   a trip mechanism coupled to the maintaining mechanism for releasing the maintaining mechanism; and
   a disarming mechanism coupled to the incising assembly for moving the incising assembly to the non-incising position from the incising position in response to release of the maintaining means.

10. The instrument of claim 2, further comprising a spring element that urges the first and second members toward the non-incising position from the incising position.

11. The instrument of claim 2, wherein the spring element exerts at least partly an axial force for causing relative helical movement between the first and second members.

12. The instrument of claim 2, wherein the spring element exerts at least partly a rotational force for causing relative helical movement between the first and second members.

13. The instrument of claim 2, further comprising an arming mechanism coupled to the incising assembly for manually moving the incising assembly to the incising position from the non-incising position.

14. A surgical instrument for incising a path in a body wall, comprising:
   an elongate sleeve extending along a longitudinal axis;
   an incising assembly carried at a distal end of the sleeve, the incising assembly comprising a first member and a second member that slidably mate and interfit for non-incising and incising positions of the first and second members, wherein in the non-incising position at least one sharp edge of the first member is capable of incising tissue and in the incising position the at least one sharp edge is not capable of incising tissue;
   a maintaining mechanism operatively connected to the incising assembly which releasably maintains the incising assembly in the incising position;
   a trip mechanism coupled to the maintaining mechanism for releasing the maintaining mechanism; and
   a disarming mechanism coupled to the incising assembly for moving the incising assembly to the non-incising position from the incising position in response to release of the maintaining mechanism.

15. The instrument of claim 14, wherein the trip mechanism includes an axially-reciprocating probe member, the probe member being retractable in a proximal direction in response to a counterforce applied to a distal end thereof and extendable in the distal direction in response to a reduction of counterforce on the distal end thereof, whereby retraction of the probe member past a particular position arms the trip mechanism and subsequent extension of the probe member past a particular position trips the trip mechanism.

16. The instrument of claim 14, further comprising a spring element operatively connected to urge the probe member in the distal direction.

17. The instrument of claim 14, the trip mechanism including a retraction-float structure, whereby the probe member when retracted proximally from an extended position to an intermediate-retracted position does not trip the trip mechanism when returned distally to the extended position.

18. The instrument of claim 14, the trip mechanism including a projection-float structure, whereby the probe member when projected distally from a retracted position to an intermediate-extended position does not trip the trip mechanism when returned proximally to the retracted position.

19. The instrument of claim 14, further comprising:
   an insufflator-accommodating structure incorporated into a proximal end of the probe member; and
   a longitudinally extending lumen within the probe member communicating between openings in proximal and distal ends thereof, the distal end including at least one aperture for allowing passage of an insufflation medium therethrough.

20. A method for incising a pathway in a body wall with an incising instrument having an incising assembly comprising first and second mating members and movable between a non-incising position and an incising position, the method comprising the steps of:
   putting the incising assembly in the incising position;
   then pressing a distal end of the instrument against a body wall;
   helically and distally advancing the incising assembly into the body wall, thereby incising a pathway in the body wall; and
   helically advancing a distal portion of the incising instrument into the body cavity with the incising assembly in the non-incising position, a helical protruding edge of the incising assembly threadably engaging tissue around the incised pathway for pulling the incising instrument distally.

21. The method of claim 20, wherein the incising assembly is carried at a distal end of a sleeve, the helically advancing step including the step of making at least one incised track in the body wall, wherein a transverse dimension of the at least one incised track is less than a transverse dimension of the sleeve.

22. The method of claim 20, further comprising the steps of:
   sensing when a distalmost end of the incising assembly has penetrated into the body cavity; and
   in response to the sensing step, disarming the incising assembly, thereby moving the incising assembly to the non-cising position from the incising position.

23. A method for incising a pathway in a body wall with an incising instrument having an incising assembly comprising first and second mating members and movable between a non-incising position and an incising position, the method comprising the steps of:

putting the incising assembly in the incising position;

then pressing a distal end of the instrument against a body wall;

helically and distally advancing the incising assembly into the body wall, thereby incising a pathway in the body wall;

sensing when the incising assembly has penetrated into a body cavity; and in response to the sensing, insufflating the body cavity with a insufflator connected to the incising instrument.

24. A method of making an incision in a body wall overlying an anatomic space, comprising the steps of:

inserting a distal end of an elongate member from the exterior of the body into an anatomic space, thereby making an incision;

contemporaneous with the inserting step, viewing an interior of the body wall from within the anatomic space, thereby insuring the incision is in a particular location; and advancing inwardly an incising instrument over the member and through the incision, the incising instrument defining a longitudinal passageway extending therethrough to accommodate the member, wherein the incising instrument incises tissue around the member, thereby increasing a transverse dimension of the incision;

wherein the advancing step includes advancing a cannula into the incision, the cannula being removably and concentrically mounted around the incising instrument, and further comprising the step of withdrawing outwardly the incising instrument from the cannula, thereby providing the cannula in communication with the anatomic space.

25. A method of making an incision in a body wall, comprising the steps of:

introducing a distal end of a member into the interior of the body at a first location;

directing the distal end of the member to a second location in the interior of body; and advancing outwardly the distal end of the member in the second location until the distal end of the member is exposed outside the body, thereby making an incision from the interior of the body to the exterior of the body at the second location; and contemporaneous with the advancing step, the step of viewing the interior of the body wall as the distal end of the member is advanced to the exterior of the body, thereby insuring the incision is in a particular location.

26. A method of making an incision in a body wall, comprising the steps of:

introducing a distal end of a member into the interior of the body at a first location;

directing the distal end of the member to a second location in the interior of body;

advancing outwardly the distal end of the member in the second location until the distal end of the member is exposed outside the body, thereby making an incision from the interior of the body to the exterior of the body at the second location; and advancing inwardly an incising instrument over the distal end of the member through the incision, the incising instrument defining a longitudinal passageway extending therethrough to accommodate the member, wherein the incising instrument incises tissue around the member, thereby increasing a transverse dimension of the incision.

27. The method of claim 26, wherein the advancing step includes advancing a cannula into the incision, the cannula being removably and concentrically mounted around the incising instrument, and further comprising the step of withdrawing outwardly the incising instrument from the cannula, thereby providing the cannula in communication with the anatomic space.

* * * * *